United States Patent
Weiss et al.

(10) Patent No.: US 10,729,684 B2
(45) Date of Patent: Aug. 4, 2020

(54) ALKYNYL DIHYDROQUINOLINE SULFONAMIDE COMPOUNDS

(71) Applicant: AMGEN INC., Thousand Oaks, CA (US)

(72) Inventors: Matthew Weiss, Boston, MA (US); Thomas Dineen, Arlington, MA (US); Karina R. Vaida, Burlington, MA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 16/062,602

(22) PCT Filed: Dec. 19, 2016

(86) PCT No.: PCT/US2016/067622
§ 371 (c)(1),
(2) Date: Jun. 14, 2018

(87) PCT Pub. No.: WO2017/106872
PCT Pub. Date: Jun. 22, 2017

(65) Prior Publication Data
US 2018/0369226 A1    Dec. 27, 2018

Related U.S. Application Data

(60) Provisional application No. 62/269,533, filed on Dec. 18, 2015.

(51) Int. Cl.
| | | |
|---|---|---|
| *C07D 215/36* | (2006.01) | |
| *A61K 31/4704* | (2006.01) | |
| *C07D 241/44* | (2006.01) | |
| *C07D 403/12* | (2006.01) | |
| *C07D 413/14* | (2006.01) | |
| *C07D 417/12* | (2006.01) | |
| *C07D 413/12* | (2006.01) | |
| *A61P 29/02* | (2006.01) | |
| *A61P 11/14* | (2006.01) | |
| *A61K 31/501* | (2006.01) | |

(52) U.S. Cl.
CPC ........ *A61K 31/4704* (2013.01); *A61K 31/501* (2013.01); *A61P 11/14* (2018.01); *A61P 29/02* (2018.01); *C07D 215/36* (2013.01); *C07D 241/44* (2013.01); *C07D 403/12* (2013.01); *C07D 413/12* (2013.01); *C07D 413/14* (2013.01); *C07D 417/12* (2013.01)

(58) Field of Classification Search
CPC combination set(s) only.
See application file for complete search history.

(56) References Cited

U.S. PATENT DOCUMENTS 8,101,647 B2    1/2012  Chafeev et al.

FOREIGN PATENT DOCUMENTS

| EP | 0 039 051 B1 | 4/1981 | |
|---|---|---|---|
| WO | 2013/134518 A1 | 9/2013 | |
| WO | 2014/201206 A1 | 12/2014 | |
| WO | WO2014201206 | * | 12/2014 |

OTHER PUBLICATIONS

Fricton et al, Can we prevent Chronic Pain, retrieved from https://www.practicalpainmanagement.com/treatments/can-we-prevent-chronic-pain, p. 1-10 (Year: 2019).*
Patani, Bioisosterism: A Rational Approach to Drug Design, 1996, Chem Rev, vol. 96, p. 3147-3176 (Year: 1996).*
S. M. Berge et al., Pharmaceutical Salts, J. Pharm Sci., vol. 66, No. 1, Jan. 1977.
Bundgaard et. al.; "A Novel Solution-Stable, Water-Soluble Prodrug Type for Drugs Containing a Hydroxyl or NH Acidic Group" Journal of Medicinal Chemistry 32; 12; 2503-2507; 1989.
Bundgaard, H.; "Design of prodrugs" Amsterdam; New York: Elsevier; New York, NY, USA: Sole distributors for the USA and Canada, Elsevier Science Pub. Co., 1985.
Chaplan, et al., Quantitative assessment of tactile allodynia in the rat paw, Journal of Neuroscience Methods, 53, 55-63, 1994.
Cox J.J., Reimann F, Nicholas A. K., et al. "An SCN9A channelopathy causes congenital inability to experience pain," Nature, vol. 444:894-898, 2006.
Dib-Hajj, et. al., The Nav1.7 sodium channel. from molecule to man, Nature Reviews Neuroscience, 14, 49-62, 2013.
Dib-Hajj, et al., NaN, a novel voltage-gated Na channel, is expressed preferentially in peripheral sensory neurons and down-regulated after axotomy, Proc. Natl. Acad. Sci. USA, 95(15):8963-8968, 1998.
Do and Bean, Subthreshold Sodium Currents and Pacemaking of Subthalamic Neurons: Modulation by Slow Inactivation, Neuron 39:109-120, 2003.
Drenth J. P. H., Morsche R. H. M., Guillet G., Taieb A., et al., "SCN9A mutations define primary erythermalgia as a neuropathic disorder of voltage gated sodium channels," J Invest Dermatol 124:1333-1338, 2005.

(Continued)

*Primary Examiner* — Karen Cheng
(74) *Attorney, Agent, or Firm* — Elsa D. Lemoine

(57) ABSTRACT

The present invention provides compounds of Formula I, and pharmaceutically acceptable salts thereof, that are inhibitors of voltage-gated sodium channels, in particular Nav1.7. The compounds are useful for the treatment of diseases associated with the activity of sodium channels such as pain disorders, cough, and itch. Also provided are pharmaceutical compositions containing compounds of the present invention.

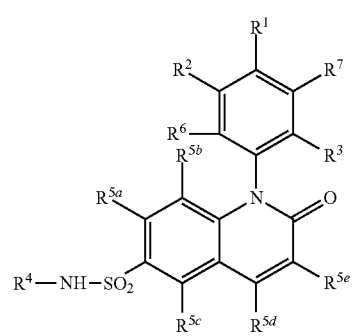

20 Claims, No Drawings

(56) References Cited

OTHER PUBLICATIONS

Ettinger and Argoff, Use of antiepileptic drugs for nonepileptic conditions: psychiatric disorders and chronic pain, Neurotherapeutics, 4:75-83, 2007.

Fertleman C. R., Baker M. D., Parker K. A., Moffatt S., et al., "SCN9A mutations in paroxysmal extreme pain disorder: allelic variants underlie distinct channel defects and phenotypes," Neuron 52:767-774, 2006.

Gillet L., et. al., Voltage-Gated sodium channel activity promotes cysteine cathepsin-dependent invasiveness and colony growth of human cancer cells, J Biol Chem, (epub) 2009.

Goldberg Y. P., MacFarlane J., MacDonald M. L., Thompson J., et al. "Loss-of-function mutations in the Nav1.7 gene underlie congenital indifference to pain in multiple human populations," Clin Genet vol. 71, Issue 4, pp. 311-319, 2007.

Goldin, A. L, "Resurgence of sodium channel research," Ann Rev Physiol 63:871-894, 2001.

Gonzalez, Termin, Wilson, Small Molecule Blockers of Voltage-gated Sodium Channels, Methods and Principles in Medicinal Chemistry, 29:168-192, 2006.

Haim, B.D., et al., Upregulation of Sodium Channel Nav1.3 and Functional Involvement in Neuronal Hyperexcitability Associated with Central Neuropathic Pain after Spinal Cord Injury, J. Neuroscience, 23(26):8881-8892, 2003.

Bethany Halford, Changing the Channel, Cen. ACS. Org., 2014.

Hamann M, Meisler MH, Richter A., Motor disturbances in mice with deficiency of the sodium channel gene Scn8a show features of human dystonia, Exp Neurol 23, 184: 830-838, 2003.

Haufe V., et. al., The promiscuous nature of the cardiac sodium current, J Mol. Cell Cardiol. 42(3):469-477, 2007.

T. Higuchi; V. Stella; ACS Symposium Series; vol. 14, Pro-drugs as Novel Delivery Systems, 1975.

Hille B, Ion Channels of Excitable Membranes, Sinauer Associates, Inc.: Sunderland MA, 3rd Ed. 2001.

International Preliminary Report of Patentability, dated, Jun. 19, 2018.

Johannessen L. C., Antiepileptic drugs in non-epilepsy disorders: relations between mechanisms of action and clinical efficacy, CNS Drugs 22(1)27-47, 2008.

Kim D. Y., et. al., BACE1 regulates voltage gated sodium channels and neuronal activity, Nat. Cell. Biol. 9 (7):755-764, 2007.

Liu, H., et al., Mutations in Cardiac Sodium Channels, Am. J. Pharmacogenomics, 3(3): 173-179, 2003.

McKinney B. C, et. al., Exaggerated emotional behavior in mice heterozygous for the sodium channel Scn8a (Nav1.6), Genes Brain Behav., 7(6):629-638, 2008.

Morinville et al., Distribution of the voltage ☐ gated sodium channel $Na_v1.7$ in the rat: Expression in the autonomic and endocrine systems, J Comp Neurol., 504:680-689, 2007.

Puopolo et al., Roles of Subthreshold Calcium Current and Sodium Current in Spontaneous Firing of Mouse Midbrain Dopamine Neurons, J. Neurosci. 27 :645-656, 2007.

Raymond, C.K., et al., Expression of Alternatively Spliced Sodium Channel—Subunit Genes: J. Biol.Chem, 279 (44):46234-46241, 2004.

Roche, Edward B. Bioreversible Carriers in Drug Design: Theory and Applications. Pergamon Press, 1987.

Svensson et. al.; The Design and Bioactivation of Presystemically Stable Prodrugs; Drug Metabolism Reviews, 19 (2) 165-194; 1988.

Tamaoka A., Paramyotonia congenita and skeletal sodium channelopathy, Internal Medicine, vol. 42, No. 9:769-770, 2003.

Waxman, Axonal conduction and injury in multiple sclerosis: the role of sodium channels, Nature Neurosci. 7 :932-941, 2006.

Wood, J. N. and Boorman, J. Voltage-gated sodium channel blockers; target validation and therapeutic potential, Curr. Top Med. Chem. 5:529-537, 2005.

Woodruff-Pak D. S., et. al., Inactivation of sodium channel SCN8A ($Na_v1.6$) in purkinje neurons impairs learning in Morris Water Maze and delay but not trace eyeblink classical conditioning, Behav. Neurosci. 120(2):229-240, 2006.

Yang Y., Wang Y., Li S, et al., Mutations in SCN9A, encoding a sodium channel alpha subunit, in patients with primary erythermalgia, J. Med. Genet. 41:171-174, 2004.

Yu, F.H., et al., Reduced sodium current in GABAergic interneurons in a mouse model of severe myoclonic epilepsy in infancy, Nat. Neuroscience, 9 (9) 1142-1149, 2006.

\* cited by examiner

US 10,729,684 B2

ALKYNYL DIHYDROQUINOLINE SULFONAMIDE COMPOUNDS

RELATED APPLICATIONS

This application is a National Stage Application under 35 U.S.C. § 371 of International Application No. PCT/US2016/67622, having an international filing date of Dec. 19, 2016, which is claiming priority from U.S. Provisional Application No. 62/269,533, having a filing date of Dec. 18, 2015.

FIELD OF THE INVENTION

The present invention provides compounds that are inhibitors of voltage-gated sodium channels (Navy), in particular Nav 1.7, and are useful for the treatment of diseases treatable by inhibition of sodium channels such as pain disorders. Also provided are pharmaceutical compositions containing compounds of the present invention.

BACKGROUND OF THE INVENTION

A 2011 report of the institute of medicine estimates that 100 million adults in the US, roughly 30% of the population, suffer from chronic pain (C & E News, Bethany Halford, "Changing the Channel", published 3-24). Chronic pain by definition involves abnormal electrical spiking of neurons in the pain pathways: peripheral sensory neurons, spinal cord neurons, neurons in the pain matrix of the brain (e.g., somatosensory cortex, insular cortex, anterior cingular cortex), and/or neurons in brainstem. Although firing of these neurons is modulated and governed by many different receptors, enzymes, and growth factors, in most neurons the fast upstroke of the electrical spike is produced by entry of sodium ions through voltage-gated sodium channels (Hille B, Ion Channels of Excitable Membranes. Sinauer Associates, Inc.: Sunderland Mass., $3^{rd}$ Ed. 2001). There are nine different isoforms of voltage-gated sodium channel (Nav 1.1-Nav 1.9), and they have distinct expression patterns in tissues including neurons and cardiac and skeletal muscle (Goldin, A. L, "Resurgence of sodium channel research," Ann Rev Physiol 63:871-894, 2001; Wood, J. N. and, Boorman, J. "Voltage-gated sodium channel blockers; target validation and therapeutic potential" Curr. Top Med. Chem. 5:529-537, 2005).

Nav1.1 and Nav1.2 are highly expressed in the brain (Raymond, C. K., et al., J. Biol. Chem. (2004) 279 (44): 46234-41) and are vital to normal brain function. Some loss of function due to Nav 1.1 mutations in humans, have resulted in epilepsy, presumably as these channels are expressed in inhibitory neurons (Yu, F. H., et al., Nat. Neuroscience (2006), 9 (9) 1142-1149). Nav1.1 is also expressed in the peripheral nervous system and inhibition of Nav1.1 in the periphery may provide relief of pain. Hence, while inhibiting Nav1.1 may provide use fro treating pain, it may also be undesirable possibly leading to anxiety and over excitability. Nav1.3 is expressed primarily in the fetal central nervous system, and expression was found to be upregulated after nerve injury in rats (Hains, B. D., et al., J. Neuroscience (2030) 23(26):8881-8892). Nav1.4 is expressed primarily in skeletal muscle. Mutations of the gene and its' product have significant impact on muscle function, including paralysis (Tamaoka A., Internal Medicine (2003), (9):769-770). Nav1.5 is expressed mainly in cardiac myocytes, including atria, ventricles, the sino-atrial node, atrio-ventircular node and cardiac Purkinje fibers. The rapid upstroke of the cardiac action potential and the rapid impulse conduction through cardiac tissue is due to the opening of the Nav1.5 channel. Mutations of the Nav1.5 channel have resulted in arrhythmic syndromes, including QTc prolongation, Brugada syndrome (BS), sudden unexpected nocturnal death syndrome (SUNDS) and sudden infant death syndrome (SIDS) (Liu, H., et al., Am. J. Pharmacogenomics (2003), 3(3):173-179). Nav1.6 is widely distributed voltage-gated sodium channel expressed throughout the central and peripheral nervous system. Nav1.8 is expressed primarily in sensory ganglia of the peripheral nervous system, such as the dorsal root ganglia. There are no identified Nav1.8 mutations that produce varied pain responses in humans. Nav1.8 differs from most neuronal Nay isotypes in that it is insensitive to inhibition by tetrodotoxin. Nav1.9, similar to Nav1.8, is also a tetrodotoxin insensitive sodium channels expressed primarily in dorsal root ganglia neurons (Dib-Hajj, S. D., et al., Proc. Natl. Acad. Sci. USA (1998), 95(15):8963-8968).

Recent evidence from several independent genetic studies has shown that the tetrodotoxin-sensitive voltage-gated sodium ion channel Nav 1.7 (SCN9A) is required to sense pain. Rare genetic forms of severe chronic pain, Primary Erythromelalgia and Paroxysmal Extreme Pain Disorder, result from mutations that increase the activity of Nav 1.7 (Fertleman C. R., Baker M. D., Parker K. A., Moffatt S., et al., "SCN9A mutations in paroxysmal extreme pain disorder: allelic variants underlie distinct channel defects and phenotypes," Neuron 52:767-774, 2006; Yang Y., Wang Y., Li S, et al., "Mutations in SCN9A, encoding a sodium channel alpha subunit, in patients with primary erythermalgia," J. Med. Genet. 41:171-174, 2004; Drenth J. P. H., te Morsche R. H. M., Guillet G., Taieb A., et al., "SCN9A mutations define primary erythermalgia as a neuropathic disorder of voltage gated sodium channels," J Invest Dermatol 124:1333-1338). Conversely, two separate clinical studies have determined that the root cause of the genetic disorder Congenital Indifference to Pain (CIP) is a loss of function of Nav 1.7 via mutations that truncate the protein and destroy function (Cox J. J., Reimann F, Nicholas A. K., et al. "An SCN9A channelopathy causes congenital inability to experience pain," Nature 444:894-898, 2006; Goldberg Y. P., MacFarlane J., MacDonald M. L., Thompson J., et al. "Loss-of-function mutations in the Nav1.7 gene underlie congenital indifference to pain in multiple human populations," Clin Genet 71:311-319, 2007). The disorder is inherited in Mendelian recessive manner with 100% penetrance. The phenotype associated with CIP is extreme: affected individuals are reported to have experienced painless burns, childbirth, appendicitis, and bone fractures, as well as to have insensitivity to clinical measures of pain such as pinprick or tendon pressure. Yet sensory, motor, autonomic, and other measured functions are normal, with the only reported abnormality being anosmia (inability to smell). These studies indicate that among the many possible targets in the pain pathway, Nav 1.7 governs one or more control points critical for pain perception.

Nonselective sodium channel inhibitors such as lidocaine, mexiletine, and carbamazepine show clinical efficacy in chronic pain, including neuropathic pain, but they are limited in dose and in use, likely due to effects on sodium channels outside the pain pathway. Lidocaine is a local anesthetic doctors use for minor surgery. Dentists use novocaine. However these compounds do not distinguish between the various sodium channel subtypes, making them unsuitable for use as systemic pain killers. "If you give a drug that blocks Nav1.7 but also blocks Nav1.5, the patient will die of heart failure," says Glenn F. King, a professor at Australia's University of Queensland who studies venoms that block ion channels. "It will be a completely painless death, but the patient will die nonetheless." Thus, selectivity for Nav1.7 is desired, particularly over Nav1.5. Researchers have tailored their efforts to find a molecule that inhibitors or block the activity of only Nav1.7. To compound this problem, the identity, every location, every function and/or the tertiary structures of each subtype of voltage gated sodium channel proteins are not known or completely understood.

Consequently, a number of researchers are attempting to identify small molecule inhibitors of Nav1.7. For example, Chafeev et al disclose spiro-oxindole compound for the treatment and/or prevention of sodium channel-mediated diseases, such as pain, in U.S. Pat. No. 8,101,647. International Publications WO 2013/134518 and WO 2014/201206 disclose sulfonamide derivatives which are different from the sulfonamide derivatives of the present invention. Thus, there is a need to identify Nav1.7 inhibitors selective over at least Nav1.5 to treat pain. The present invention provides compounds that are selective inhibitors of Nav 1.7. over at least Nav1.5.

SUMMARY OF THE INVENTION

In embodiment 1, the present invention provides a compound of Formula (I), an enantiomer, diastereoisomer, atropisomer thereof, or a mixture thereof, or a pharmaceutically acceptable salt thereof,

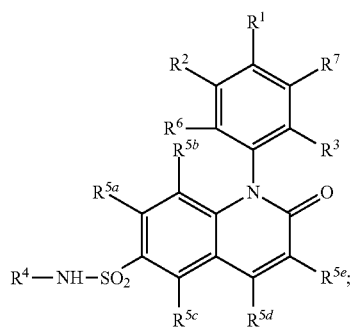

(I)

wherein:

$R^1$ is an ethynyl substituted by an $C_{1-8}$alk or a 3- to 10-membered-saturated, -partially saturated, or -unsaturated-carbocyclic or -heterocyclic ring containing 0, 1, 2, or 3 heteroatoms selected from N, O, or S; wherein said $C_{1-8}$alk is substituted by 0, 1, 2, 3, or 4 $R^8$ groups selected from halo, —OH, —OC$_{1-4}$alk, —NH$_2$, —NHC$_{1-4}$alk, —OC(=O)C$_{1-4}$alk, or —N(C$_{1-4}$alk)C$_{1-4}$alk; and wherein said -carbocyclic, or -heterocyclic ring is substituted by 0, 1, 2, 3, or 4 $R^9$ groups selected from halo, —OH, —C$_{1-4}$alk, —C$_{1-4}$haloalk, —OC$_{1-4}$alk, —OC$_{1-4}$haloalk, —NH$_2$, —NHC$_{1-4}$alk, —OC(=O)C$_{1-4}$alk, or —N(C$_{1-4}$alk)C$_{1-4}$alk;

$R^2$ is H, halo, $C_{1-6}$alk, or $C_{1-6}$haloalk;

$R^3$ is —O—$C_{1-6}$alk;

$R^4$ is a 5- to 6-membered heteroaryl;

Each of $R^6$ and $R^7$ is hydrogen; and

Each of $R^{5a}$; $R^{5b}$; $R^{5c}$; $R^{5d}$; and $R^{5e}$ is independently hydrogen or halo.

In embodiment 2, the present invention provides compounds of Formula (I), an enantiomer, diastereoisomer, atropisomer thereof, or a mixture thereof, or a pharmaceutically acceptable salt thereof, wherein $R^1$ is ethynyl substituted by an $C_{1-6}$alk or a 3- to 6-membered-saturated carbocyclic ring; wherein said $C_{1-6}$alk is substituted by 0, 1, 2, 3, or 4 $R^8$, which is halo; and said -carbocyclic ring is substituted by 0, 1, 2, 3, or 4 $R^9$ groups selected from halo, —C$_{1-4}$alk, —C$_{1-4}$haloalk, —OC$_{1-6}$alk, or —OC$_{1-6}$haloalk. In a sub-embodiment of embodiment 2, the 3- to 6-membered-saturated carbocyclic ring is selected from cyclopropyl, cyclobutyl, cyclopentyl, or cyclohexyl; wherein each said carboxylic ring is substituted by 0, 1, 2, 3, or 4 $R^9$ groups selected from F, Cl, —CF$_3$, or —O—CH$_2$—CF$_3$.

In embodiment 3, the present invention provides compounds of Formula (I), an enantiomer, diastereoisomer, atropisomer thereof, or a mixture thereof, or a pharmaceutically acceptable salt thereof, wherein $R^1$ is selected from —C≡C—CF$_3$, —C≡C—C(CH$_3$)$_2$—CF$_3$, —C≡C— cyclopropyl-CF$_3$, —C≡C-cyclopentyl (wherein said cyclopentyl is unsubstituted or is substituted by —O—CH$_2$—CF$_3$), or —C≡C-cyclohexyl- (wherein said cyclohexyl is substituted by 2 F atoms).

In embodiment 4, the present invention provides compounds of Formula (I), an enantiomer, diastereoisomer, atropisomer thereof, or a mixture thereof, or a pharmaceutically acceptable salt thereof, wherein $R^2$ is H, fluoro, chloro, methyl, CF$_3$, CHF$_2$, or CH$_2$F. In a sub-embodiment of embodiment 4, is H or fluoro. In a further sub-embodiment of embodiment 4, $R^2$ is fluoro.

In embodiment 5, the present invention provides compounds of Formula (I), an enantiomer, diastereoisomer, atropisomer thereof, or a mixture thereof, or a pharmaceutically acceptable salt thereof, wherein $R^3$ is methoxy.

In embodiment 6, the present invention provides compounds of Formula (I), an enantiomer, diastereoisomer, atropisomer thereof, or a mixture thereof, or a pharmaceutically acceptable salt thereof, wherein $R^4$ is a 5-membered heteroaryl.

In embodiment 7, the present invention provides compounds of Formula (I), an enantiomer, diastereoisomer, atropisomer thereof, or a mixture thereof, or a pharmaceutically acceptable salt thereof, wherein $R^4$ is a 6-membered heteroaryl.

In embodiment 8, the present invention provides compounds of Formula (I), an enantiomer, diastereoisomer, atropisomer thereof, or a mixture thereof, or a pharmaceutically acceptable salt thereof, wherein $R^4$ is isoxazolyl, pyridazinyl, isoxazolyl, thiazolyl, thiadiazolyl, pyridazinyl, pyridyl, or pyrimidinyl. In a sub embodiment of embodiment 8, $R^4$ is isoxazolyl or pyridazinyl. In another sub embodiment of embodiment 8, $R^4$ is isoxazolyl.

In embodiment 9, the present invention provides compounds of Formula (I), an enantiomer, diastereoisomer, atropisomer thereof, or a mixture thereof, or a pharmaceutically acceptable salt thereof, wherein each of $R^{5a}$; $R^{5b}$; $R^{5c}$; $R^{5d}$; and $R^{5e}$ is hydrogen.

In embodiment 10, the present invention provides compounds of Formula (I), an enantiomer, diastereoisomer, atropisomer thereof, or a mixture thereof, or a pharmaceutically acceptable salt thereof, which is:

| Ex. | Structure | Chemical Name |
|---|---|---|
| 1 | 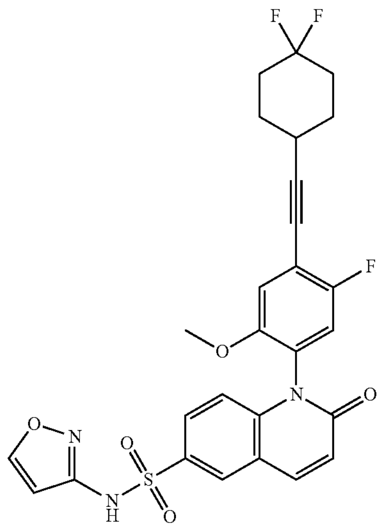 [SMILES: COc1cc(C#CC2CCC(F)(F)CC2)c(F)cc1-n1c(=O)ccc2cc(S(=O)(=O)Nc3ccon3)ccc21] | 1-(4-((4,4-difluorocyclohexyl)ethynyl)-5-fluoro-2-methoxyphenyl)-N-3-isoxazolyl-2-oxo-1,2-dihydro-6-quinolinesulfonamide |
| 2 | 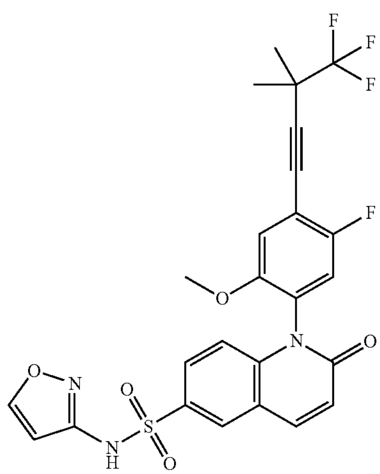 [SMILES: COc1cc(C#CC(C)(C)C(F)(F)F)c(F)cc1-n1c(=O)ccc2cc(S(=O)(=O)Nc3ccon3)ccc21] | 1-(5-fluoro-2-methoxy-4-(4,4,4-trifluoro-3,3-dimethyl-1-butyn-1-yl)phenyl)-N-3-isoxazolyl-2-oxo-1,2-dihydro-6-quinolinesulfonamide |
| 3 | 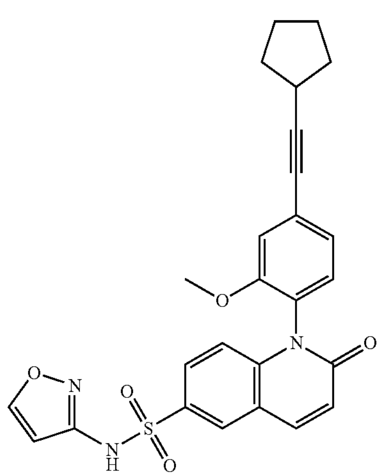 [SMILES: COc1cc(C#CC2CCCC2)ccc1-n1c(=O)ccc2cc(S(=O)(=O)Nc3ccon3)ccc21] | 1-(4-(cyclopentylethynyl)-2-methoxyphenyl)-N-3-isoxazolyl-2-oxo-1,2-dihydro-6-quinolinesulfonamide |

-continued

| Ex. | Structure | Chemical Name |
|---|---|---|
| 4A | 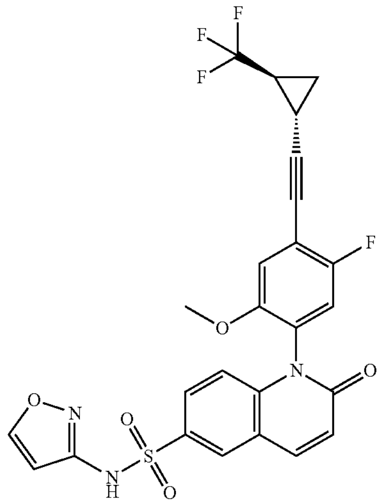 [SMILES: COc1cc(C#C[C@H]2C[C@@H]2C(F)(F)F)c(F)cc1-n1c(=O)ccc2cc(S(=O)(=O)Nc3ccon3)ccc21] | 1-(5-fluoro-2-methoxy-4-(((1R,2S)-2-(trifluoromethyl)cyclopropyl)ethynyl)phenyl)-N-3-isoxazolyl-2-oxo-1,2-dihydro-6-quinolinesulfonamide, 1-(5-fluoro-2-methoxy-4-(((1S,2S)-2-(trifluoromethyl)cyclopropyl)ethynyl)phenyl)-N-3-isoxazolyl-2-oxo-1,2-dihydro-6-quinolinesulfonamide |
| 4B | 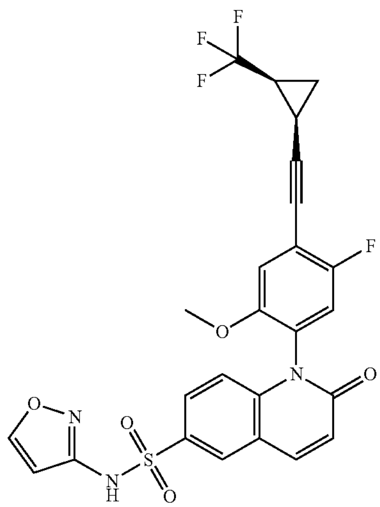 [SMILES: COc1cc(C#C[C@@H]2C[C@@H]2C(F)(F)F)c(F)cc1-n1c(=O)ccc2cc(S(=O)(=O)Nc3ccon3)ccc21] | 1-(5-fluoro-2-methoxy-4-(((1R,2S)-2-(trifluoromethyl)cyclopropyl)ethynyl)phenyl)-N-3-isoxazolyl-2-oxo-1,2-dihydro-6-quinolinesulfonamide |
| 5 | 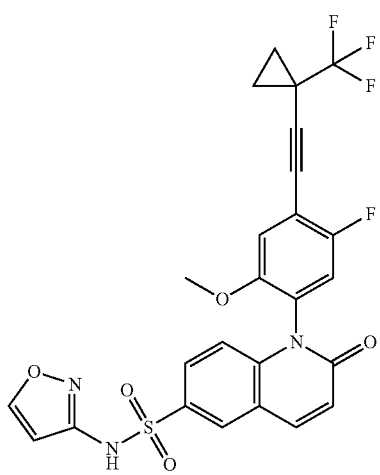 [SMILES: COc1cc(C#CC2(C(F)(F)F)CC2)c(F)cc1-n1c(=O)ccc2cc(S(=O)(=O)Nc3ccon3)ccc21] | 1-(5-fluoro-2-methoxy-4-(((1R,2R)-2-(trifluoromethyl)cyclopropyl)ethynyl)phenyl)-N-3-isoxazolyl-2-oxo-1,2-dihydro-6-quinolinesulfonamide |

-continued

| Ex. | Structure | Chemical Name |
|---|---|---|
| 6 | 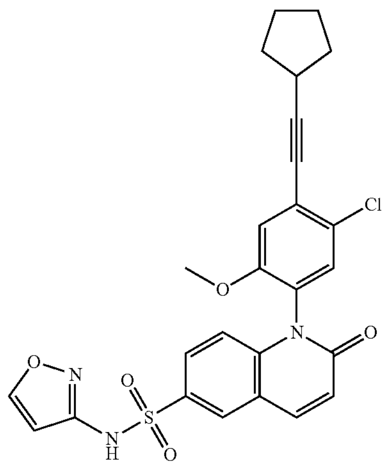 [SMILES: COc1cc(C#CC2CCCC2)c(Cl)cc1-n1c(=O)ccc2cc(S(=O)(=O)Nc3ccon3)ccc21] | 1-(5-fluoro-2-methoxy-4-((1-(trifluoromethyl)cyclopropyl)ethynyl)phenyl)-N-3-isoxazolyl-2-oxo-1,2-dihydro-6-quinolinesulfonamide |
| 7 | 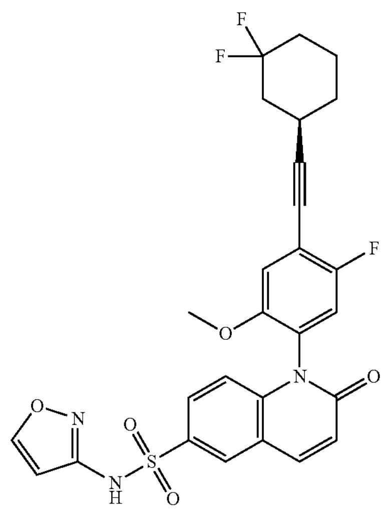 [SMILES: COc1cc(C#C[C@@H]2CCCC(F)(F)C2)c(F)cc1-n1c(=O)ccc2cc(S(=O)(=O)Nc3ccon3)ccc21] | 1-(5-chloro-4-(cyclopentylethynyl)-2-methoxyphenyl)-N-3-isoxazolyl-2-oxo-1,2-dihydro-6-quinolinesulfonamide |

-continued

| Ex. | Structure | Chemical Name |
|---|---|---|
| 8 | 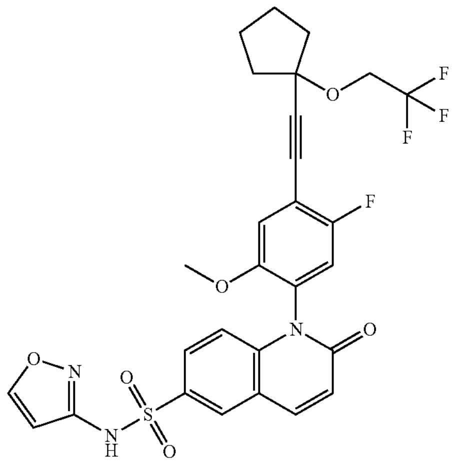 [SMILES: COc1cc(C#CC2(OCC(F)(F)F)CCCC2)c(F)cc1-n1c(=O)ccc2cc(S(=O)(=O)Nc3ccon3)ccc21] | 1-(4-(((1R)-3,3-difluorocyclohexyl)ethynyl)-5-fluoro-2-methoxyphenyl)-N-3-isoxazolyl-2-oxo-1,2-dihydro-6-quinolinesulfonamide, 1-(4-(((1S)-3,3-difluorocyclohexyl)ethynyl)-5-fluoro-2-methoxyphenyl)-N-3-isoxazolyl-2-oxo-1,2-dihydro-6-quinolinesulfonamide |
| 9 | 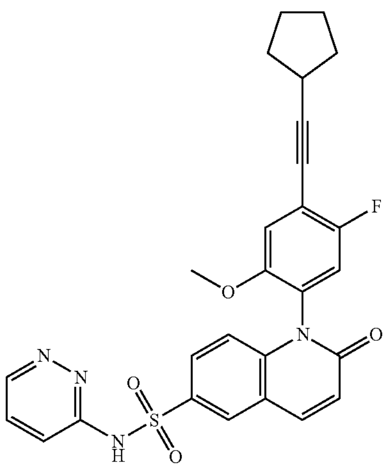 [SMILES: COc1cc(C#CC2CCCC2)c(F)cc1-n1c(=O)ccc2cc(S(=O)(=O)Nc3cccnn3)ccc21] | 1-(5-fluoro-2-methoxy-4-((1-(2,2,2-trifluoroethoxy)cyclopentyl)ethynyl)phenyl)-N-3-isoxazolyl-2-oxo-1,2-dihydro-6-quinolinesulfonamide |
| 10 | 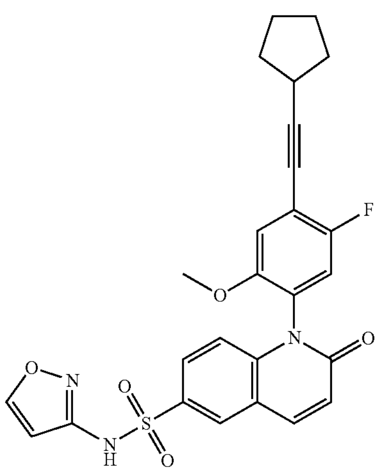 [SMILES: COc1cc(C#CC2CCCC2)c(F)cc1-n1c(=O)ccc2cc(S(=O)(=O)Nc3ccon3)ccc21] | 1-(4-(cyclopentylethynyl)-5-fluoro-2-methoxyphenyl)-2-oxo-N-3-pyridazinyl-1,2-dihydro-6-quinolinesulfonamide |

In embodiment 10a, the present invention provides a compound of Formula (I), which is 1-(4-((4,4-difluorocyclohexyl)ethynyl)-5-fluoro-2-methoxyphenyl)-N-3-isoxazolyl-2-oxo-1,2-dihydro-6-quinolinesulfonamide, or an enantiomer, diastereoisomer, atropisomer thereof, or a mixture thereof, or a pharmaceutically acceptable salt thereof.

In embodiment 10b, the present invention provides a compound of Formula (I), which is 1-(5-fluoro-2-methoxy-4-(4,4,4-trifluoro-3,3-dimethyl-1-butyn-1-yl)phenyl)-N-3-isoxazolyl-2-oxo-1,2-dihydro-6-quinolinesulfonamide, or an enantiomer, diastereoisomer, atropisomer thereof, or a mixture thereof, or a pharmaceutically acceptable salt thereof.

In embodiment 10c, the present invention provides a compound of Formula (I), which is 1-(4-(cyclopentylethynyl)-2-methoxyphenyl)-N-3-isoxazolyl-2-oxo-1,2-dihydro- 6-quinolinesulfonamide, or an enantiomer, diastereoisomer, atropisomer thereof, or a mixture thereof, or a pharmaceutically acceptable salt thereof.

In embodiment 10d, the present invention provides a compound of Formula (I), which is 1-(5-fluoro-2-methoxy-4-(((1R,2S)-2-(trifluoromethyl)cyclopropyl)ethynyl)phenyl)-N-3-isoxazolyl-2-oxo-1,2-dihydro-6-quinolinesulfonamide, or an enantiomer, diastereoisomer, atropisomer thereof, or a mixture thereof, or a pharmaceutically acceptable salt thereof.

In embodiment 10e, the present invention provides a compound of Formula (I), which is 1-(5-fluoro-2-methoxy-4-(((1S,2S)-2-(trifluoromethyl)cyclopropyl)ethynyl)phenyl)-N-3-isoxazolyl-2-oxo-1,2-dihydro-6-quinolinesulfonamide, or an enantiomer, diastereoisomer, atropisomer thereof, or a mixture thereof, or a pharmaceutically acceptable salt thereof.

In embodiment 10f, the present invention provides a compound of Formula (I), which is 1-(5-fluoro-2-methoxy-4-(((1R,2R)-2-(trifluoromethyl)cyclopropyl)ethynyl)phenyl)-N-3-isoxazolyl-2-oxo-1,2-dihydro-6-quinolinesulfonamide, or an enantiomer, diastereoisomer, atropisomer thereof, or a mixture thereof, or a pharmaceutically acceptable salt thereof.

In embodiment 10g, the present invention provides a compound of Formula (I), which is 1-(5-fluoro-2-methoxy-4-((1-(trifluoromethyl)cyclopropyl)ethynyl)phenyl)-N-3-isoxazolyl-2-oxo-1,2-dihydro-6-quinolinesulfonamide, or an enantiomer, diastereoisomer, atropisomer thereof, or a mixture thereof, or a pharmaceutically acceptable salt thereof.

In embodiment 10h, the present invention provides a compound of Formula (I), which is 1-(5-chloro-4-(cyclopentylethynyl)-2-methoxyphenyl)-N-3-isoxazolyl-2-oxo-1,2-dihydro-6-quinolinesulfonamide, or an enantiomer, diastereoisomer, atropisomer thereof, or a mixture thereof, or a pharmaceutically acceptable salt thereof.

In embodiment 10i, the present invention provides a compound of Formula (I), which is 1-(4-(((1R)-3,3-difluorocyclohexyl)ethynyl)-5-fluoro-2-methoxyphenyl)-N-3-isoxazolyl-2-oxo-1,2-dihydro-6-quinolinesulfonamide, or an enantiomer, diastereoisomer, atropisomer thereof, or a mixture thereof, or a pharmaceutically acceptable salt thereof.

In embodiment 10j, the present invention provides a compound of Formula (I), which is 1-(4-(((1S)-3,3-difluorocyclohexyl)ethynyl)-5-fluoro-2-methoxyphenyl)-N-3-isoxazolyl-2-oxo-1,2-dihydro-6-quinolinesulfonamide, or an enantiomer, diastereoisomer, atropisomer thereof, or a mixture thereof, or a pharmaceutically acceptable salt thereof.

In embodiment 10k, the present invention provides a compound of Formula (I), which is 1-(5-fluoro-2-methoxy-4-((1-(2,2,2-trifluoroethoxy)cyclopentyl)ethynyl)phenyl)-N-3-isoxazolyl-2-oxo-1,2-dihydro-6-quinolinesulfonamide, or an enantiomer, diastereoisomer, atropisomer thereof, or a mixture thereof, or a pharmaceutically acceptable salt thereof.

In embodiment 10l, the present invention provides a compound of Formula (I), which is 1-(4-(cyclopentylethynyl)-5-fluoro-2-methoxyphenyl)-N-3-isoxazolyl-2-oxo-1,2-dihydro-6-quinolinesulfonamide, or an enantiomer, diastereoisomer, atropisomer thereof, or a mixture thereof, or a pharmaceutically acceptable salt thereof.

In embodiment 11, the present invention provides a P atropisomer of each individual compound, independently, or a mixture thereof, or pharmaceutically acceptable salts thereof, recited in embodiments 10a to 10l.

In embodiment 12, the present invention provides an M atropisomer of each individual compound, independently, or a mixture thereof, or pharmaceutically acceptable salts thereof, recited in embodiments 10a to 10l.

In embodiment 13, the present invention provides pharmaceutical compositions comprising a compound, an enantiomer, diastereoisomer, atropisomer thereof, or a mixture thereof, or pharmaceutically acceptable salts thereof, in accordance with any one of embodiments 1, 2, 3, 4, 5, 6, 7, 8, 9, 10, 10a to 10l, 11, and 12, and a pharmaceutically acceptable excipient.

In embodiment 14, the present invention provides methods of treating pain, cough, or itch, the methods comprising administering to a patient in need thereof a therapeutically effective amount of a compound, an enantiomer, diastereoisomer, atropisomer thereof, or a mixture thereof, or pharmaceutically acceptable salts thereof, in accordance with any one of embodiments 1, 2, 3, 4, 5, 6, 7, 8, 9, 10, 10a to 10l, 11, and 12.

In embodiment 15, the present invention provides methods of embodiment 14 wherein the pain is selected from chronic pain, acute pain, neuropathic pain, pain associated with rheumatoid arthritis, pain associated with osteoarthritis, pain associated with cancer, cancer, or pain associated with diabetes.

In embodiment 16, the present invention provides methods of embodiment 14 wherein the cough is selected from post viral cough, viral cough, or acute viral cough. See Dib-Hajj. et. al., "The Nav1.7 sodium channel: from molecule to man", *Nature Reviews Neuroscience* (2013), 14, 49-62.

DETAILED DESCRIPTION OF THE INVENTION

The present invention provides compounds of Formula (I), as defined above, an enantiomer, diastereoisomer, atropisomer thereof, or a mixture thereof, or pharmaceutically acceptable salts thereof. The present invention also provides pharmaceutical compositions comprising a compound of Formula (I), compound, an enantiomer, diastereoisomer, atropisomer thereof, or a mixture thereof, or pharmaceutically acceptable salts thereof, and methods of treating diseases and/or conditions, such as pain, using compounds of Formula (I), compound, an enantiomer, diastereoisomer, atropisomer thereof, or a mixture thereof, or pharmaceutically acceptable salts thereof.

The term "$C_{\alpha-\beta}alk$" means an alkyl group comprising a minimum of $\alpha$ and a maximum of $\beta$ carbon atoms in a branched or linear relationship or any combination of the two, wherein $\alpha$ and $\beta$ represent integers. A designation of $C_0alk$ indicates a direct bond. Examples of $C_{1-6}alk$ include, but are not limited to the following:

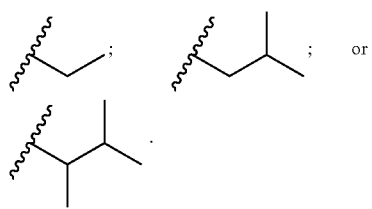

The term "halo" or "halogen" means a halogen atoms selected from F, Cl, Br or I.

The term "$C_{\alpha-\beta}$haloalk" means an alk group, as defined herein, in which at least one of the hydrogen atoms has been replaced with a halo atom, as defined herein. Common $C_{\alpha-\beta}$haloalk groups are $C_{1-3}$fluoroalk. An example of a common $C_{1-3}$fluoroalk group is —$CF_3$.

The term "alkynyl" as used herein, alone or in combination, refers to an optionally substituted straight-chain or optionally substituted branched-chain hydrocarbon group having one or more carbon-carbon triple-bonds and having from two to about ten carbon atoms, more preferably from two to about six carbon atoms, as well as those having from two to about four carbon atoms. Examples of alkynyl group include ethynyl, 2-propynyl, 2-butynyl, 1,3-butadiynyl and the like.

The term "heteroatom" as used herein means an oxygen, nitrogen or sulfur atom.

The term "aryl" means a cyclic, aromatic hydrocarbon. Examples of aryl groups include phenyl and naphthyl. Common aryl groups are six to thirteen membered rings.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heteroatoms are particularly common.

The term "diastereoisomer" generally refers to any group of four optical isomers occurring in compounds containing two asymmetric carbon atoms or two optically active centers, as defined in Gessner G. Hawley (ed.), The Condensed Chemical Dictionary, 10th Edition, Van Nostrand Reinhold Company Inc., New York, 1981, 1135 pp.

The term "pharmaceutically acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. For additional examples of "pharmacologically acceptable salts," and Berge et al., J. Pharm. Sci. 66:1 (1977).

The term "substituted" means that a hydrogen atom on a molecule or group is replaced with a group or atom. Typical substitutents include: halogen, $C_{1-8}$alkyl, hydroxyl, $C_{1-8}$alkoxy, —$NR^xR^x$, nitro, cyano, halo or perhalo$C_{1-8}$alkyl, $C_{2-8}$alkenyl, $C_{2-8}$alkynyl, —$SR^x$, —$S(=O)_2R^x$, —$C(=O)OR^x$, —$C(=O)R^x$, wherein each $R^x$ is independently hydrogen or $C_1$-$C_8$ alkyl. It is noted that when the substituent is —$NR^xR^x$, the $R^x$ groups may be joined together with the nitrogen atom to form a ring.

A group or atom that replaces a hydrogen atom is also called a substituent.

Any particular molecule or group can have one or more substituent depending on the number of hydrogen atoms that can be replaced.

The term "unsubstituted" means a hydrogen atom on a molecule or group. The term "substituted" means that a hydrogen atom on a molecule or group is replaced with a group or atom. Typical substituents include: halogen, $C_{1-8}$alkyl, hydroxyl, $C_{1-8}$alkoxy, —$NR^xR^x$, nitro, cyano, halo or perhalo$C_{1-8}$alkyl, $C_{2-8}$alkenyl, $C_{2-8}$alkynyl, —$SR^x$, —$S(=O)_2R^x$, —$C(=O)OR^x$, —$C(=O)R^x$, wherein each $R^x$ is independently hydrogen or $C_1$-$C_8$ alkyl. It is noted that when the substituent is —$NR^xR^x$, the $R^x$ groups may be joined together with the nitrogen atom to form a ring.

The symbol "-" represents a covalent bond and can also be used in a radical group to indicate the point of attachment to another group. In chemical structures, the symbol is commonly used to represent a methyl group in a molecule.

The term "leaving group" generally refers to groups readily displaceable by a nucleophile, such as an amine, a thiol or an alcohol nucleophile, or by metallic agent such as boronic acids or boronates under transition metal catalyzed coupling conditions. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

The term "protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted aromatic heterocyclyl groups (Y'=O, S, NR), and the like, which are illustrated in the following examples:

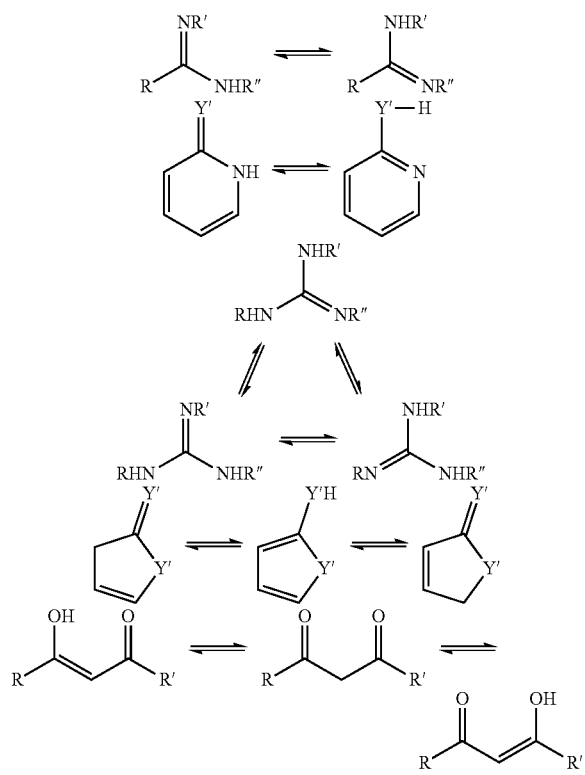

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, 4/11/81) discloses Mannich-base hydroxamic acid prodrugs, their preparation and use.

The term "therapeutically effective amount" means an amount of a compound that ameliorates, attenuates or eliminates one or more symptom of a particular disease or condition, or prevents or delays the onset of one of more symptom of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of Formula I, or a salt of a compound of Formula I, or a formulation containing a compound of Formula I, or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered by a tablet, while another is administered by injection or orally as syrup. All combinations, delivery methods and administration sequences are contemplated.

The compounds of the present invention may be used in the manufacture of a medicament for the treatment of a disease and/or condition mediated by Nav 1.7, such as pain, chronic cough or itch.

Pain is typically divided into primary types: chronic and acute pain based on the duration of the pain. Typically, chronic pain lasts for longer than 3 months. Examples of chronic pain include pain associated with rheumatoid arthritis, osteoarthritis, lumbosacral radiculopathy or cancer. Chronic pain also includes idiopathic pain, which is pain that has no identified cause. An example of idiopathic pain is fibromyalgia.

Another type of pain is nociceptive pain. Nociceptive pain is caused by stimulation of peripheral nerve fibers that respond to highly noxious events such as thermal, mechanical or chemical stimuli.

Still another type of pain is neuropathic pain. Neuropathic pain is pain that is caused by damage or disease affecting a part of the nervous system. Phantom limb pain is a type of neuropathic pain. In phantom limb pain, the body detects pain from a part of a body that no longer exists. For example, a person who has had a leg amputated may feel leg pain even though the leg no longer exists.

In one embodiment of the methods of treatment provided by the present invention using the compounds of Formula (I), or pharmaceutically acceptable salts thereof, the disease is chronic pain. In another aspect, the chronic pain is associated with, but are not limited to, post-herpetic neuralgia (shingles), rheumatoid arthritis, osteoarthritis, diabetic neuropathy, complex regional pain syndrome (CRPS), cancer or chemotherapy-induced pain, chronic back pain, phantom limb pain, trigeminal neuralgia, HIV-induced neuropathy, cluster headache disorders, and migraine, primary erythromelalgia, and paroxysmal extreme pain disorder. Other indications for Nav 1.7 inhibitors include, but are not limited to, depression (Morinville et al., *J Comp Neurol.*, 504:680-689 (2007)), bipolar and other CNS disorders (Ettinger and Argoff, *Neurotherapeutics*, 4:75-83 (2007)), epilepsy: ibid., and Gonzalez, Termin, Wilson, Methods and Principles in Medicinal Chemistry, 29:168-192 (2006)), multiple sclerosis (Waxman, *Nature Neurosci.* 7:932-941 (2006)), Parkinson's (Do and Bean, *Neuron* 39:109-120 (2003); Puopolo et al., *J. Neurosci.* 27:645-656 (2007)), restless legs syndrome, ataxia, tremor, muscle weakness, dystonia, tetanus (Hamann M., et. al., *Exp. Neurol.* 184(2): 830-838, 2003), anxiety, depression: McKinney B. C, et. al., *Genes Brain Behav.* 7(6):629-638, 2008), learning and memory, cognition (Woodruff-Pak D. S., et. al., *Behav. Neurosci.* 120(2):229-240, 2006), cardiac arrhythmia and fibrillation, contractility, congestive heart failure, sick sinus syndrome (Haufe V., et. al., *J Mol. Cell Cardiol.* 42(3):469-477, 2007), schizophrenia, neuroprotection after stroke, drug and alcohol abuse (Johannessen L. C., *CNS Drugs* 22(1)27-47, 2008), Alzheimer's (Kim D. Y., et. al., *Nat. Cell. Biol.* 9(7):755-764, 2007), and cancer (Gillet L., et. al., *J Biol Chem* 2009, January 28 (epub)).

Another aspect of the invention relates to a method of treating acute and/or chronic inflammatory and neuropathic pain, dental pain, general headache, migraine, cluster headache, mixed-vascular and non-vascular syndromes, tension headache, general inflammation, arthritis, rheumatic diseases, rheumatoid arthritis, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to the present invention. A preferred type of pain to be treated is chronic neuropathic pain. Another preferred type of pain to be treated is chronic inflammatory pain.

In another aspect of the invention, the compounds of the present invention can be used in combination with other compounds that are used to treat pain. Examples of such other compounds include, but are not limited to aspirin, celecoxib, hydrocodone, oxycodone, codeine, fentanyl, ibuprofen, ketoprofen, naproxen, acetaminophen, gabapentin and pregabalin. Examples of classes of medicines that contain compounds that can be used in combination with the compounds of the present invention include non-steroidal anti-inflammatory compounds (NSAIDS), steroidal compounds, cycloxogenase inhibitors and opiod analgesics.

The compounds of the present invention may also be used to treat diabetes, obesity and/or to facilitate weight loss.

The compounds of the present invention may be used in combination with other pharmaceutically active compounds. It is noted that the term "pharmaceutically active compounds" can include biologics, such as proteins, antibodies and peptibodies.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed by said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, cocrystyals, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$) alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, a-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

In addition, if a compound of the present invention comprises a sulfonamide moiety, a prodrug can be formed by replacement of the sulfonamide N(H) with a group such as —CH$_2$P(O)(O($C_1$-$C_6$)alkyl)$_2$ or —CH$_2$OC(O)($C_1$-$C_6$) alkyl.

The compounds of the present invention also include tautomeric forms of prodrugs.

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as S and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can can also be separated by converting the enantiomeric mixture into a diastereomeric mixture by reaction with an appropriate optically active compound (e.g., an alcohol), separating the diastereomers and converting (e.g., hydrolyzing) the individual diastereomers to the corresponding pure enantiomers.

The compounds of general formula (I) may also exist in the form of atropisomers. Atropisomers are compounds with identical structural formulae, but which have a particular spatial configuration resulting from a restricted rotation around a single bond, due to a major steric hindrance on either side of this single bond. Atropisomerism is independent of the presence of stereogenic elements, such as an asymmetric carbon. The terms "P atropisomer" or "M atropisomer" are used herein in order to be able to clearly name two atropisomers of the same pair. For example, the following compound of Intermediate B1, Step 1, having the structure below can be separated into the pair of atropisomers P and M via a chiral column:

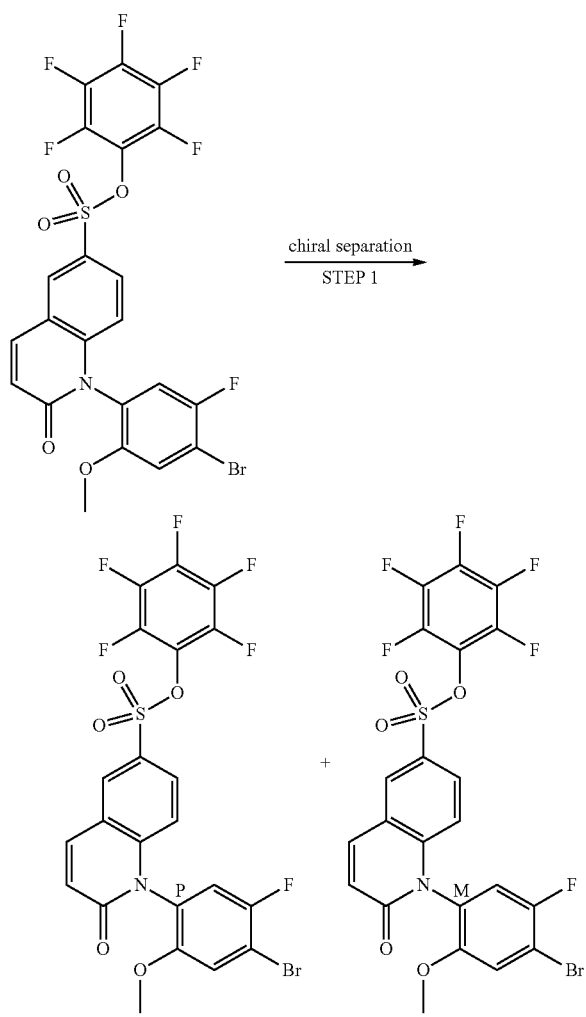

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the tetrazole moiety are included in this invention. Also, for example, all keto-enol or imine-enamine forms of the compounds are included in this invention. Other examples of tautomerism are as follows:

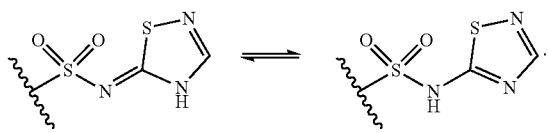 [SMILES: *S(=O)(=O)/N=c1/[nH]cns1 ; *S(=O)(=O)Nc1ncns1]

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{31}P$, $^{32}P$, $^{35}S$, $^{18}F$, and $^{36}Cl$. In another aspect, the compounds of the present invention contain one or more deuterium atoms (2H) in place of one or more hydrogen atoms.

Compounds of the present invention that contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detection. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

All patents and other publications recited herein are hereby incorporated by reference in their entirety.

The examples presented below illustrate specific embodiments of the present invention. These examples are meant to be representative and are not intended to limit the scope of the claims in any manner.

It is noted that when a percent (%) is used with regard to a liquid, it is a percent by volume with respect to the solution. When used with a solid, it is the percent with regard to the solid composition. Materials obtained from commercial suppliers were typically used without further purification. Reactions involving air or moisture sensitive reagents were typically performed under a nitrogen or argon atmosphere. Purity was measured using high performance liquid chromatography (HPLC) system with UV detection at 254 nm and 215 nm (System A: Agilent Zorbax Eclipse XDB-C8 4.6×150 mm, 5 μm, 5 to 100% CH$_3$CN in H$_2$O with 0.1% TFA for 15 min at 1.5 mL/min; System B: Zorbax SB-C8, 4.6×75 mm, 10 to 90% CH$_3$CN in H$_2$O with 0.1% formic acid for 12 min at 1.0 mL/min) (Agilent Technologies, Santa Clara, Calif.). Silica gel chromatography was generally performed with prepacked silica gel cartridges (Biotage, Uppsala, Sweden or Teledyne-Isco, Lincoln, Nebr.). $^{1}$H NMR spectra were recorded on a Bruker AV-400 (400 MHz) spectrometer (Bruker Corporation, Madison, Wis.) or a Varian (Agilent Technologies, Santa Clara, Calif.) 400 MHz spectrometer at ambient temperature. All observed protons are reported as parts per million (ppm) downfield from tetramethylsilane (TMS) or other internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series (Agilent Technologies, Santa Clara, Calif.) LC/MS with UV detection at 254 nm and 215 nm and a low resonance electrospray mode (ESI).

SYNTHETIC EXAMPLES

The following list of abbreviations used or commonly used throughout the specification represent the following and should assist in understanding the invention:
ACN, MeCN acetonitrile
Aq., aq. aqueous
Ar argon (gas)
BOP benzotriazol-1-yl-oxy Hexafluorophosphate
BuLi Butyllithium
$Cs_2CO_3$ cesium carbonate
$CHCl_3$ chloroform
$CH_2Cl_2$, DCM dichloromethane, methylene chloride
Cu(1)I copper(1) iodide
DCC dicyclohexylcarbodiimide
DIC 1,3-diisopropylcarbodiimide
DIEA, DIPEA diisopropylethylamine
DME dimethoxyethane
DMF dimethylformamide
DMAP 4-dimethylaminopyridine
DMS dimethylsulfide
DMSO dimethylsulfoxide
EDC, EDCI 1-(3-dimethylaminopropyl)-3-ethylcarbodiimide
$Et_2O$ diethyl ether
EtOAc ethyl acetate
FBS fetal bovine serum
G, gm gram
h, hr hour
$H_2$ hydrogen
$H_2O$ water
HCl hydrochloric acid
HOAc acetic acid
HPLC high pressure liquid chromatography
IPA, IpOH isopropyl alcohol
$K_2CO_3$ potassium carbonate
KI potassium iodide
LG leaving group
LDA Lithium diisopropylamide
LiOH lithium hydroxide
$MgSO_4$ magnesium sulfate
MS or m/z mass spectrum
MeOH methanol
$N_2$ nitrogen
$NaCNBH_3$ sodium cyanoborohydride
$Na_2CO_3$ sodium carbonate
$NaHCO_3$ sodium bicarbonate
NaH sodium hydride
NaI sodium iodide
$NaBH_4$ sodium borohydride
NaOH sodium hydroxide
$Na_2SO_4$ sodium sulfate
$NH_4Cl$ ammonium chloride
$NH_4OH$ ammonium hydroxide
$P(t-bu)_3$ tri(tert-butyl)phosphine
PBS phosphate buffered saline
Pd/C palladium on carbon
$Pd(PPh_3)_4$ palladium(0)triphenylphosphine tetrakis
$Pd(dppf)Cl_2$ palladium(1,1-bisdiphenylphosphinoferrocene)(II)chloride
$Pd(PhCN)_2Cl_2$ palladium di-cyanophenyl dichloride
$Pd(OAc)_2$ palladium acetate
$Pd_2(dba)_3$ tris(dibenzylideneacetone) dipalladium
RT, rt room temperature
RBF, rbf round bottom flask
TLC, tlc thin layer chromatography
TEA, $Et_3N$ triethylamine
TFA trifluoroacetic acid
THF tetrahydrofuran The following preparations of compounds of Formula (I) and intermediate compounds are given to enable those skilled in the art to more clearly understand and to practice the present invention. They should not be considered as limiting the scope of the invention, but merely as being illustrative and representative thereof.

Preparation of Alkyne Intermediates A1 to A5

Intermediate A1:
1-ethynyl-1-(trifluoromethyl)cyclopropane

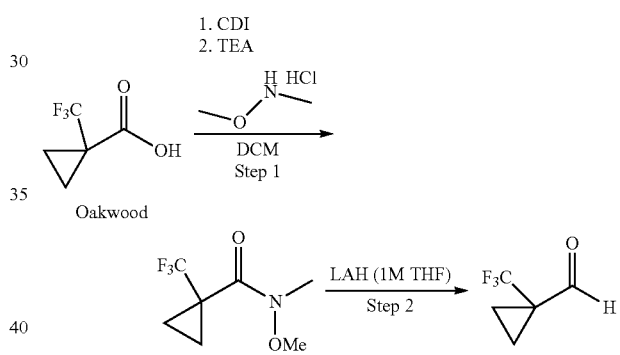

Step 1: N-methoxy-N-methyl-1-(trifluoromethyl)cyclopropanecarboxamide

To a stirred solution of 1-(trifluoromethyl)cyclopropanecarboxylic acid (1.5 g, 9.73 mmol) in DCM (48.7 mL) at 10° C., was added CDI (2.368 g, 14.60 mmol), in three portions over 5 minutes. The mixture was stirred for 30 minutes, then TEA (2.99 mL, 21.42 mmol) and N,O-dimethylhydroxylamine hydrochloride (1.899 g, 19.47 mmol) were added. The reaction mixture was stirred at room temperature for 48 hours. Analysis by LC-MS and TLC (with KMNO4 staining) shows complete conversion to product.

The reaction was diluted with 1N HCl and dichloromethane. The organic portion was washed with Aq. $NaHCO_3$ and then collected. This was concentrated and purified in 10-50% EtOAc/Heptanes to give N-methoxy-N-methyl-1-(trifluoromethyl)cyclopropanecarboxamide (1.1 g, 5.58 mmol, 57.3% yield). MS m/z=198 (M+H).

Step 2:
1-(trifluoromethyl)cyclopropanecarbaldehyde

To a chilled solution of N-methoxy-N-methyl-1-(trifluoromethyl)cyclopropanecarboxamide (1.3 g, 6.59 mmol) in THF (13.19 mL), under nitrogen atmosphere, was added lithium aluminum hydride (1M in THF) (6.14 mL, 6.14 mmol) dropwise via syringe. The resulting mixture was stirred at 0° C. for 45 minutes. Analysis by LC-MS showed complete consumption of the starting material. The mixture was then cooled to −5° C. and treated with a 2M aqueous solution of potassium bisulfate (13.95 mL, 13.95 mmol) drop-wise via pipette. The mixture was stirred vigorously for 30 minutes. The mixture was then diluted with MTBE. The organic layer was collected and concentrated to give the pure aldehyde (250 mg, 1.81 mmol, 27.5% yield). ¹HNMR (400 MHz, CHLOROFORM-d) δ ppm 9.70 (s, 1H) 1.40-1.48 (m, 4H).

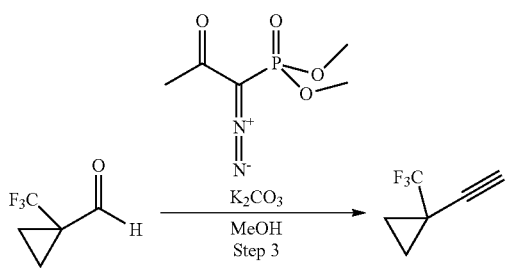

Step 3: 1-ethynyl-1-(trifluoromethyl)cyclopropane

To a mixture of 1-(trifluoromethyl)cyclopropanecarbaldehyde (500 mg, 3.62 mmol) in methanol (6 mL) was added potassium carbonate (1 g, 7.24 mmol). The resulting mixture was cooled to 0° C. and treated with a solution of Ohira-Bestmann reagent (0.652 mL, 4.35 mmol) in 1 mL of MeOH. The mixture was stirred for 2 hours and then diluted with ethyl acetate and water. The organic portion was collected, dried over sodium sulfate and concentrated carefully to give the acetylene. 1H NMR (400 MHz, CHLOROFORM-d) δ ppm 2.66-2.70 (m, 1H) 1.40-1.46 (m, 4H).

Intermediate A2:
4,4,4-trifluoro-3,3-dimethylbut-1-yne

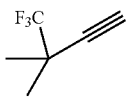

The title compound was prepared in an analogous manner to that of INTERMEDIATE A1, except that 3,3,3-trifluoro-2,2-dimethylpropanoic acid was used in step 1 instead of 1-(trifluoromethyl)cyclopropanecarboxylic acid. INTERMEDIATE A2 was isolated as a clear oil.

Intermediate A3:
trimethyl((2-(trifluoromethyl)cyclopropyl)ethynyl)silane

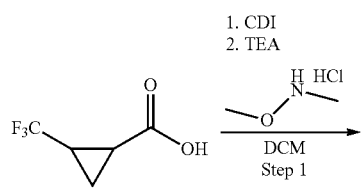

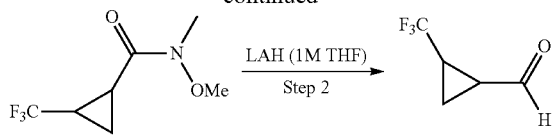

Step 1: N-methoxy-N-methyl-2-(trifluoromethyl)cyclopropanecarboxamide

To a stirred solution of 2-(trifluoromethyl)cyclopropanecarboxylic acid (cis and trans mixture) (2 g, 12.98 mmol) in DCM (19.97 mL) at 10° C., was added CDI (3.16 g, 19.47 mmol), in three portions over 5 minutes. The resulting mixture was stirred for 30 minutes. TEA (3.98 mL, 28.6 mmol) and N,O-dimethyl hydroxylamine hydrochloride (2.53 g, 26.0 mmol) were then added. The reaction mixture was stirred at room temperature for 18 hours. The mixture was cooled to 0° C. and quenched by adding 3N HCl solution. The organic portion was collected and washed sequentially with Aq. sodium bicarbonate solution and water. The organic portion was collected, concentrated and purified in 5-50% EtOAc/Heptanes to give N-methoxy-N-methyl-2-(trifluoromethyl)cyclopropanecarboxamide (660 mg, 3.35 mmol, 25.8% yield). MS m/z=198 (M+H).

Step 2:
2-(trifluoromethyl)cyclopropanecarbaldehyde

To a solution of N-methoxy-N-methyl-2-(trifluoromethyl)cyclopropanecarboxamide (0.66 g, 3.35 mmol) in THF (16.74 mL) at 0° C., was added a solution of lithium aluminum hydride (3.68 mL, 3.68 mmol) drop-wise. The resulting mixture was stirred at 0° C. for 45 minutes. Analysis by LC-MS showed complete consumption of the starting material. The mixture was cooled to −5° C. and treated with potassium bisulfate (Aq. 1M) (9 mL, 8.34 mmol) drop-wise. This was stirred vigorously for 30 minutes. The mixture was then diluted with MTBE. The organic layer was collected and concentrated to give the pure aldehyde.

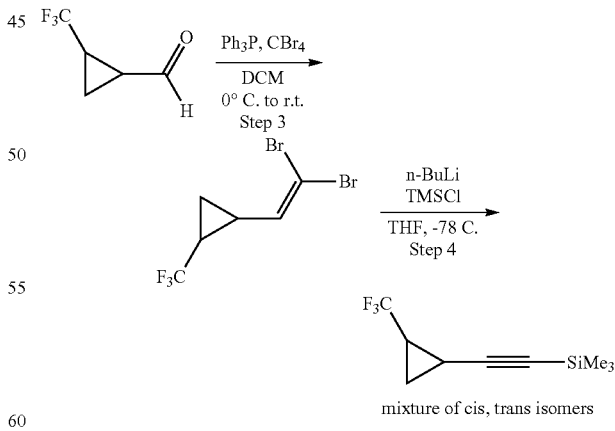

Step 3: 1-(2,2-dibromovinyl)-2-(trifluoromethyl)cyclopropane

A solution of triphenylphosphine (3.19 g, 12.17 mmol) and dichloromethane (15.21 mL) was stirred at 0° C. for 5 minutes. Carbon tetrabromide (2.017 g, 6.08 mmol) was then added portion-wise and the reaction mixture was stirred at 0° C. for 30 minutes. The resulting heterogeneous orange mixture was treated with a solution of 2-(trifluoromethyl) cyclopropanecarbaldehyde (0.42 g, 3.04 mmol) in 2 mL of DCM. The mixture was warmed up to room temp over an hour and stirred for 2 hours. The reaction was treated with 20 mL of heptanes and the resulting mixture was stirred vigorously for 1 hour. The resulting brown precipitate was collected and the filtrate was concentrated to give a clear oil. This was diluted in 10% DCM/Heptanes and concentrated. The resulting precipitate was removed and the filtrate concentrated to give 4-(2,2-dibromovinyl)-1,1-difluorocyclohexane as an orange oil (820 mg, 2.80 mmol, 92% yield).

Step 4: trimethyl((2-(trifluoromethyl)cyclopropyl)ethynyl)silane

To a solution of 1-(2,2-dibromovinyl)-2-(trifluoromethyl)cyclopropane (0.410 g, 1.395 mmol) in tetrahydrofuran (6.97 mL) at −78° C., was added n-butyllithium (2.5M in heptanes; 1.395 mL, 3.49 mmol) dropwise via syringe. The resulting mixture was stirred at −78° C. for 40 minutes. TLC analysis at this time showed complete disappearance of the starting material. To the reaction mixture was then added trimethylchlorosilane (0.624 mL, 4.88 mmol) dropwise via syringe. The reaction was warmed to ambient temperature over 30 minutes and stirred for 1 hour. The mixture was then diluted with ether and water. The organic portion was collected, concentrated to half its volume and passed through a pad of silica gel. This was then concentrated to give cis and trans mixture isomers of trimethyl((2-(trifluoromethyl)cyclopropyl)ethynyl)silane (180 mg, 0.873 mmol, 62.6% yield). (180 mg, 0.873 mmol, 62.6% yield). ¹HNMR (400 MHz, CHLOROFORM-d) δ ppm 1.85-2.15 (m, 2H), 1.61-1.68 (m, 2H), 0.51 (s, 9H).

Intermediate A4: ((4,4-difluorocyclohexyl)ethynyl)trimethylsilane

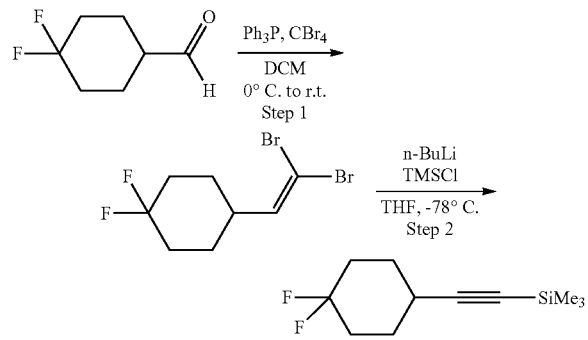

The title compound was prepared in an analogous manner to that of INTERMEDIATE A3, except that 4,4-difluorocyclohexanecarbaldehyde (purchased from Matrix Scientific) was used in Step 3 instead of 1-(trifluoromethyl)cyclopropanecarbaldehyde. INTERMEDIATE A4 (1.07 g, 4.95 mmol, 93% yield) was isolated as yellow oil. ¹HNMR (400 MHz, CHLOROFORM-d) δ ppm 2.57-2.64 (m, 1H), 2.03-2.18 (m, 2H), 1.74-1.92 (m, 6H), 0.22 (s, 9H).

Intermediate A5: 3-ethynyl-1,1-difluorocyclohexane

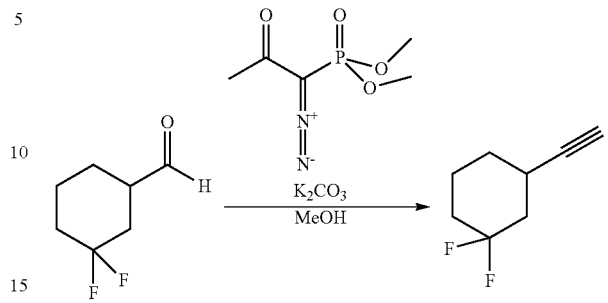

The title compound was prepared in an analogous manner to that of INTERMEDIATE A1, except that 3,3-difluorocyclohexanecarbaldehyde (Purchased from Enamine) was used in Step 3 instead of 1-(trifluoromethyl)cyclopropanecarbaldehyde. INTERMEDIATE A5 was isolated as a clear oil.

Preparation of Intermediates B1-B4

Intermediate B1: Racemic Perfluorophenyl 1-(4-bromo-5-fluoro-2-methoxyphenyl)-2-oxo-1,2-dihydro quinoline-6-sulfonate

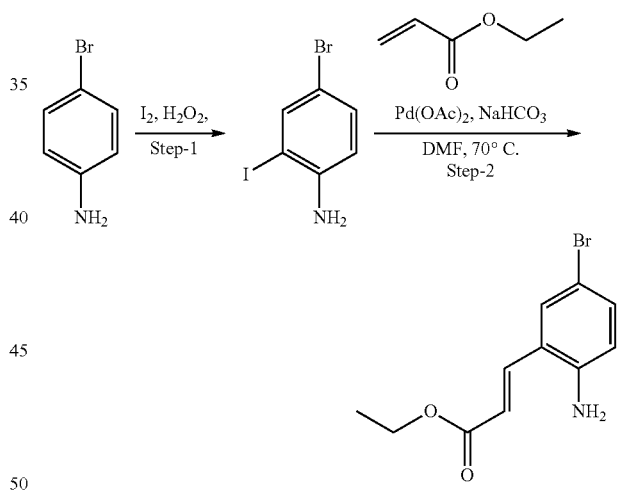

Step-1: 4-bromo-2-iodoaniline

To a solution of 4-bromo-aniline (500 g, 2.90 mol, 2.0 equiv, Saibain Chem) in cyclohexane (2.5 L) was added iodine (368 g, 1.45 mol, 1.0 equiv, Qualigens) and the mixture was heated at 50° C. After 30 min, the reaction mixture became homogenous. 30% aqueous hydrogen peroxide solution (250 mL, Spectrochem) was added to the reaction mixture. The reaction was heated for 4 h at 50° C. The reaction was cooled to room temperature, diluted with ethyl acetate (5.0 L) and washed with aqueous sodium-sulphite (2.5 Kg in 4.0 L) solution. The organic layer was washed with water (3.0 L) and brine (3.0 L) dried over magnesium sulfate, filtered and concentrated under reduced pressure to obtain the crude material which was purified by column chromatography (silica gel; mesh size 60-120, elution 0-20% ethyl acetate and hexanes) to get 4-bromo-2-iodoaniline (650 g, 75.0%), as off white solid. TLC solvent system: 100% hexanes. Product's $R_f$: 0.6. MS (ESI, positive ion) m/z: 297.0 (M+1). $^1$H NMR (400 MHz, CDCl$_3$) δ 7.72 (d, J=2.5 Hz, 1H), 7.23 (dd, J=8.4, 2.1 Hz, 1H), 6.62 (d, J=8.3 Hz, 1H), 4.09 (s, 2H).

Step-2: Ethyl (E)-3-(2-amino-5-bromophenyl)acrylate

To a solution of 4-bromo-2-iodoaniline (750 g, 2.51 mol, 1.0 equiv) in DMF (5.0 L) was added ethyl acrylate (277 g, 2.76 mol, 1.1 equiv, Avra) and sodium bicarbonate (680 g, 6.29 mol, 2.5 equiv). The reaction mixture was degassed with nitrogen for 20 min followed by the addition of palladium acetate (28.8 g, 128.27 mmol, 0.05 equiv, Hindustan Platinum). The reaction mixture was heated at 70° C. for 3h. The reaction was filtered through CELITE® and the CELITE® bed was washed with ethyl acetate (2×500 mL). The filtrate was concentrated under reduced pressure to obtain the crude residue which was purified by column chromatography (silica gel; mesh size 60-120, elution 0-20% ethyl acetate in hexanes) to obtain (E)-ethyl 3-(2-amino-5-bromophenyl)acrylate (620 g, 77.0%), as yellow solid. TLC solvent system: 20% ethyl acetate in hexanes. Product's $R_f$: 0.4. MS (ESI, positive ion) m/z; 270.2 (M+1). $^1$H NMR (400 MHz, DMSO) δ 7.75 (d, J=16.1 Hz, 1H), 7.57 (d, J=2.0 Hz, 1H), 7.16 (dd, J=9.1, 2.4 Hz, 1H), 6.66 (d, J=8.6 Hz, 1H), 6.43 (d, J=8.6 Hz, 1H), 5.81 (s, 2H), 4.20 (q, J=7.2 Hz, 2H), 1.27 (t, J=7.2 Hz, 3H).

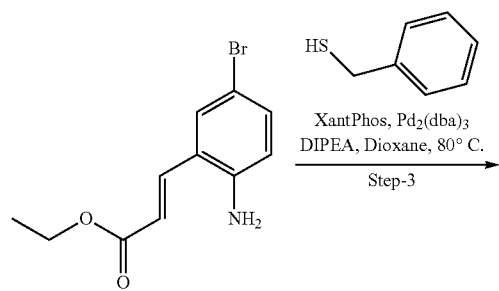

Step-3: Ethyl (E)-3-(2-amino-5-(benzylthio)phenyl)acrylate

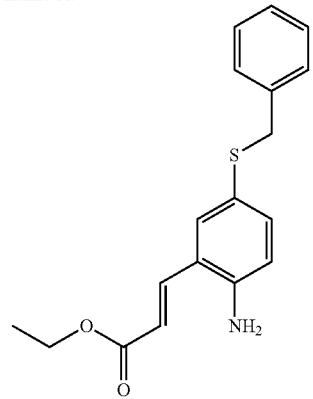

To a solution of (E)-ethyl 3-(2-amino-5-bromophenyl)acrylate (620 g, 2.29 mol, 1.0 equiv) in 1,4-dioxane (4.0 L) was added DIPEA (1.26 L, 8.88 mol, 3.9 equiv, GLR) and degassed with nitrogen for 20 mins. XantPhos (92.9 g, 106 mmol, 0.05 equiv, GLR), and tris(dibenzylideneacetone)dipalladium (84 g, 91.0 mmol, 0.04 equiv, Hindustan Platinum) was added to the reaction mixture. The mixture was purged with nitrogen and heated to 80° C. for 30 mins. The reaction was cooled to RT and benzyl mercaptan (455.5 g, 3.67 mol, 1.6 equiv, Alfa Aesar) was added and the reaction was heated at 80° C. for an additional 4 h. The reaction was cooled to room temperature and diluted with ethyl acetate (4.0 L). The mixture was filtered through CELITE® and the CELITE® bed was washed with ethyl acetate (2×1.0 L). The filtrate was concentrated under reduced pressure to obtain the crude material which was purified by chromatography (silica gel; mesh size 60-120, elution 0-40% ethyl acetate and petroleum ether) to obtain (E)-ethyl 3-(2-amino-5-(benzylthio)phenyl)acrylate (520 g, 72.0%), as yellow solid. TLC solvent system: 30% ethyl acetate in hexanes. Product's $R_f$: 0.4. MS (ESI, positive ion) m/z: 314.1 (M+1). $^1$H NMR (400 MHz, DMSO) δ 7.79 (d, J=16.1 Hz, 1H), 7.37 (d, J=2.0 Hz, 1H), 7.25-7.17 (m, 5H) 7.10 (dd, J=8.4, 2.1 Hz, 1H), 6.61 (d, J=8.3 Hz, 1H), 6.32 (d, J=15.2 Hz, 1H), 5.75 (s, 2H), 4.20 (q, J=7.2 Hz, 2H), 4.01 (s, 2H), 1.27 (t, J=7.2 Hz, 3H).

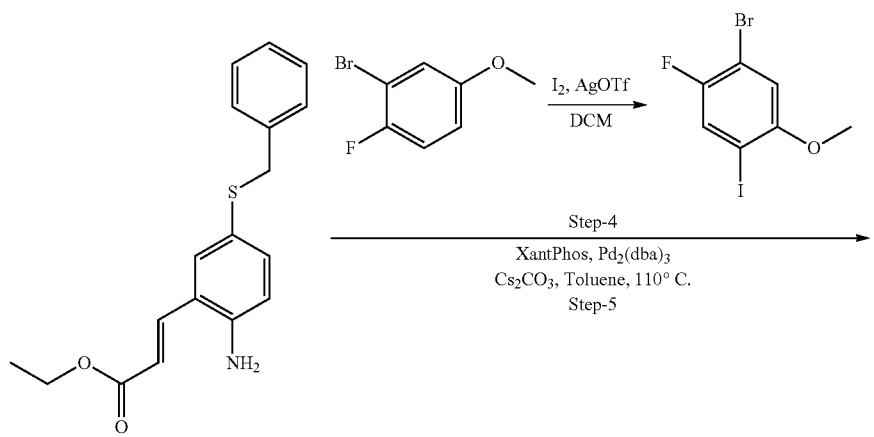

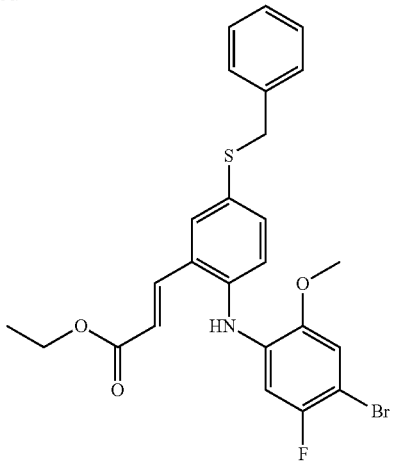

Step-4: 1-bromo-2-fluoro-4-iodo-5-methoxybenzene

To a solution of 2-bromo-1-fluoro-4-methoxybenzene (500.0 g, 2.44 mol, 1.0 equiv) in DCM (5.0 L) was added silver trifluoromethane sulfonate (686.0 g, 2.68 mol, 1.1 equiv, Angene) and the reaction mixture was stirred for 20 mins. Iodine (678.0 g, 2.68 mol, 1.1 equiv) was added to the reaction and the mixture was stirred at room temperature for 16h. The mixture was diluted with DCM (3.0 L) and filtered through CELITE®. The CELITE bed was washed with DCM (2×1.0 L) and the filtrate was washed with 20% aqueous sodium thiosulfate (3.0 L) and saturated aqueous sodium bicarbonate solution (3.0 L). The organic layer was dried over sodium sulfate, filtered and concentrated under reduced pressure to obtain the crude material which was purified by chromatography (silica gel; mesh size 60-120, elution 0-5% ethyl acetate and petroleum ether) to get 1-bromo-2-fluoro-4-iodo-5-methoxybenzene (720 g, 87%), as off-white solid. TLC solvent system: 100% hexanes. Product's $R_f$: 0.6. MS (ESI, positive ion) m/z: 331.0 (M+1). $^1$H NMR (400 MHz, CDCl$_3$) δ 7.55 (d, J=7.2 Hz, 1H), 6.95 (d, J=5.6 Hz, 1H), 3.89 (s, 3H).

Step-5: Ethyl (E)-3-(5-(benzylthio)-2-((4-bromo-5-fluoro-2-methoxyphenyl)amino)phenyl) acrylate To a solution of (E)-ethyl 3-(2-amino-5-(benzylthio)phenyl)acrylate (300 g, 958.1 mmol, 1.0 equiv) and 1-bromo-2-fluoro-4-iodo-5-methoxybenzene (348.0 g, 1051.6 mmol, 1.1 equiv) in toluene (2.5 L) was added Cs$_2$CO$_3$ (468 g, 1436.3 mmol, 1.5 equiv, Spectrochem) and the mixture was degassed with nitrogen for 20 mins. Pd$_2$(dba)$_3$ (35 g, 38.2 mmol, 0.04 equiv, Hindustan Platinum) and XantPhos (44.6 g, 76.4 mmol, 0.08 equiv, GLR) were added to the reaction mixture and the mixture was heated at 110° C. for 5h. The reaction mixture was allowed to cool to room temperature, diluted with dichloromethane (2.0 L) and filtered through CELITE® The filtrate was concentrated under reduced pressure to obtain the crude material which was purified by stirring with 5% ethyl acetate in hexanes (3.0 L) for 30 min and filtered to obtain (E)-ethyl 3-(5-(benzylthio)-2-((4-bromo-5-fluoro-2-methoxyphenyl)amino)phenyl)acrylate (350 g, 71%) as yellow solid. TLC solvent system: 30% ethyl acetate in hexanes. Product's $R_f$: 0.5. MS (ESI, positive ion) m/z; 516.2 (M+1). $^1$H NMR (400 MHz, DMSO) δ 7.73-7.61 (m, 3H), 7.34-7.15 (m, 6H), 7.02 (d, J=11.4 Hz, 1H), 6.60 (d, J=21.2 Hz, 1H), 6.33 (d, J=14.1 Hz, 1H), 4.26 (s, 2H), 4.16-4.09 (m, 2H), 3.81 (s, 3H), 1.22 (t, J=7.2 Hz, 3H). Note: NH proton not observed.

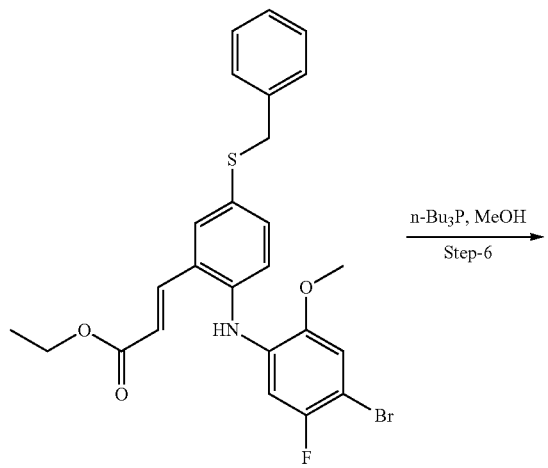

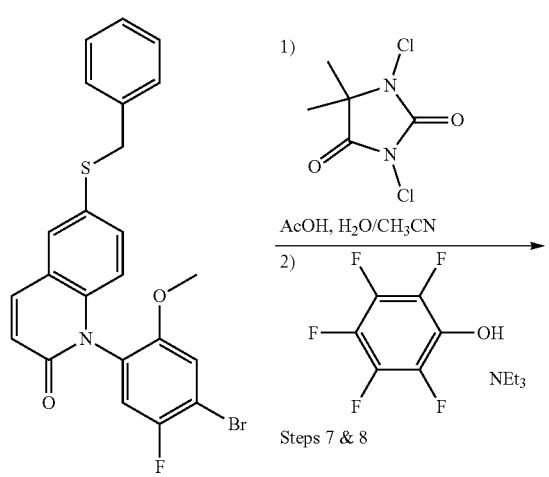

Step-6: 6-(benzylthio)-1-(4-bromo-5-fluoro-2-methoxyphenyl)quinolin-2(1H)-one

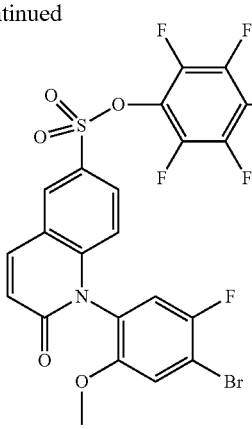

To a solution of (E)-ethyl 3-(5-(benzylthio)-2-((4-bromo-5-fluoro-2-methoxyphenyl)amino)phenyl)acrylate (250.0 g, 484.0 mmol, 1.0 equiv) in methanol (2.5 L) was added tri(n-butyl)phosphine (50% solution in ethyl acetate, 48.9 mL, 96.8 mmol, 0.2 equiv, Spectrochem) and the reaction mixture was heated at 70° C. for 5 h. The reaction mixture was allowed to cool to rt, concentrated under reduced pressure to obtain the crude material which was purified by stirring with 5% ethyl acetate in hexanes (1.0 mL) and filtered to obtain 6-(benzylthio)-1-(4-bromo-5-fluoro-2-methoxyphenyl)quinolin-2(1H)-one (201.0 g, 88%) as off white solid. TLC solvent system: 30% ethyl acetate in hexanes. Product's $R_f$: 0.3. MS (ESI, positive ion) m/z; 470.0 (M+1). $^1$H NMR (400 MHz, DMSO) δ 7.92 (d, J=9.1 Hz, 1H), 7.79 (d, J=1.7 Hz, 1H), 7.65 (d, J=6.1 Hz, 1H), 7.57 (d, J=8.8 Hz, 1H), 7.40-7.22 (m, 6H), 6.68 (d, J=9.6 Hz, 1H), 6.56 (d, J=8.8 Hz, 1H), 4.24 (s, 2H), 3.69 (s, 3H).

Steps 7 & 8: Perfluorophenyl 1-(4-bromo-5-fluoro-2-methoxyphenyl)-2-oxo-1,2-dihydro quinoline-6-sulfonate To a solution of 6-(benzylthio)-1-(4-bromo-5-fluoro-2-methoxyphenyl)quinolin-2(1H)-one (250.0 g, 531.5 mmol, 1.0 equiv) in acetonitrile (2.5 L) were added acetic acid (200 mL) and water (130 mL). The resulting mixture was cooled to 0° C. and 1,3-dichloro-5,5-dimethylimidazolidine-2,4-dione (188.5 g, 956.7 mmol, 1.8 equiv, Aldrich) was added portion-wise over 20 min keeping the internal temperature below 5° C. The resulting suspension was stirred at 0-5° C. under nitrogen for 45 min. Then a solution of pentafluorophenol (127.2 g, 690.95 mmol, 1.3 equiv, Apollo) in acetonitrile (200 mL) was added over 5 min followed by NEt$_3$ (307.7 mL, 2.12 mol, 4.0 equiv) over 20 min keeping the internal temperature below 5° C. The mixture was continued to be stirred at 0-5° C. for 30 min. Water (4.0 L) was added and extracted with ethyl acetate (2×2.0 L). The organic layer was washed with brine (1.0 L), dried over sodium sulfate, filtered and concentrated under reduced pressure to obtain the crude which was purified by stirring with isopropyl alcohol:hexanes (1:1, 1.0 L) and filtered to obtain racemic perfluorophenyl 1-(4-bromo-5-fluoro-2-methoxyphenyl)-2-oxo-1,2-dihydroquinoline-6-sulfonate (190 g, 60%) as white solid. TLC solvent system: 30% ethyl acetate in pet ether, Product's $R_f$: 0.4. MS (ESI, positive ion) m/z; 594.2 (M+1).

$^1$H-NMR (400 MHz, DMSO) δ 8.60 (d, J=2.0 Hz, 1H), 8.26 (d, J=9.8 Hz, 1H), 7.95 (dd, J=2.2, 9.1 Hz, 1H), 7.70 (t, J=8.6 Hz, 2H), 6.95-6.88 (m, 2H), 3.72 (s, 3H).

Intermediate B2: (P)-1-(4-bromo-5-fluoro-2-methoxyphenyl)-N-(isoxazol-3-yl)-2-oxo-1,2-dihydroquinoline-6-sulfonamide

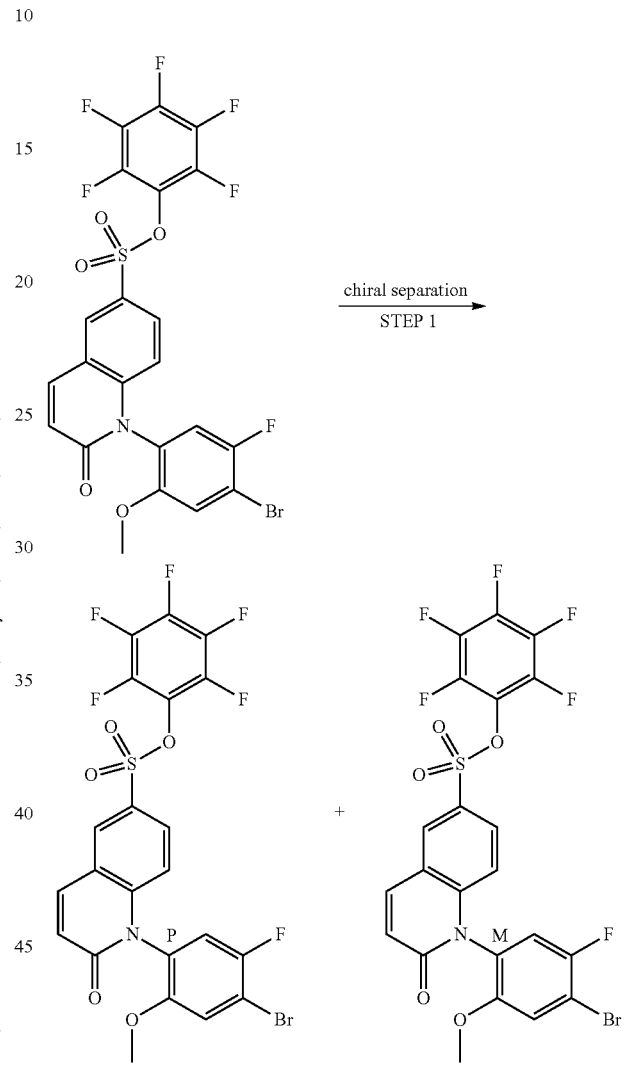

Step 1: (P)-perfluorophenyl 1-(4-bromo-5-fluoro-2-methoxyphenyl)-2-oxo-1,2-dihydroquinoline-6-sulfonate Racemic perfluorophenyl 1-(4-bromo-5-fluoro-2-methoxyphenyl)-2-oxo-1,2-dihydroquinoline-6-sulfonate (See INTERMEDIATE B1 above, 76.90 g) was separated via Chiralcel OJ column (40% MeOH/60% CO$_2$) to give (P)-perfluorophenyl 1-(4-bromo-5-fluoro-2-methoxyphenyl)-2-oxo-1,2-dihydroquinoline-6-sulfonate and (M)-perfluorophenyl 1-(4-bromo-5-fluoro-2-methoxyphenyl)-2-oxo-1,2-dihydroquinoline-6-sulfonate as pale yellow flocculent solids. Data for peak 1: m/z (ESI) 594.0 (M+H)$^+$. Data for peak 2: m/z (ESI) 594.0 (M+H)$^+$.

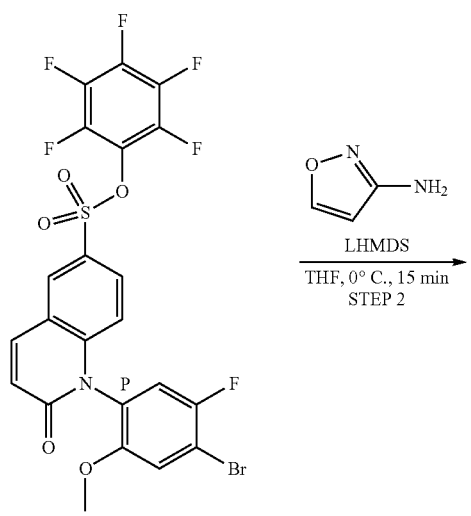

Step 2: (P)-1-(4-bromo-5-fluoro-2-methoxyphenyl)-N-(isoxazol-3-yl)-2-oxo-1,2-dihydroquinoline-6-sulfonamide A THF (200 mL) solution of (P)-perfluorophenyl 1-(4-bromo-5-fluoro-2-methoxyphenyl)-2-oxo-1,2-dihydroquinoline-6-sulfonate (6.00 g, 10.10 mmol) and 3-aminoisoxazole (0.821 ml, 11.11 mmol) in a 250-mL round-bottom flask was cooled to 0° C., and lithium bis(trimethylsilyl)amide, 1.0 M solution in THF (21.20 ml, 21.20 mmol) was added dropwise. After stirring the yellow solution at 0° C. for 15 min, it was quenched at 0° C. with 1 N HCl and extracted thrice with EtOAc. The organic extracts were combined, dried over MgSO$_4$, filtered, and concentrated to a light tan residue. Et$_2$O was added, and the slurry was titurated and sonicated. Filtration afforded an off-white solid, which was washed twice with Et$_2$O and dried in vacuo to afford 3.88 g of product as an off-white solid. The filtrate was concentrated in vacuo and purified via column chromatography (12 g silica gel, 35% to 100% EtOAc/hept gradient) to afford an additional 1.36 g of product as a pale yellow flocculent solid. A total of 5.24 g of (P)-1-(4-bromo-5-fluoro-2-methoxyphenyl)-N-(isoxazol-3-yl)-2-oxo-1,2-dihydroquinoline-6-sulfonamide was afforded. m/z (ESI) 494.1 (M+H)$^+$.

Intermediate B3: (P)-perfluorophenyl 1-(4-bromo-5-chloro-2-methoxyphenyl)-2-oxo-1,2-dihydroquinoline-6-sulfonate

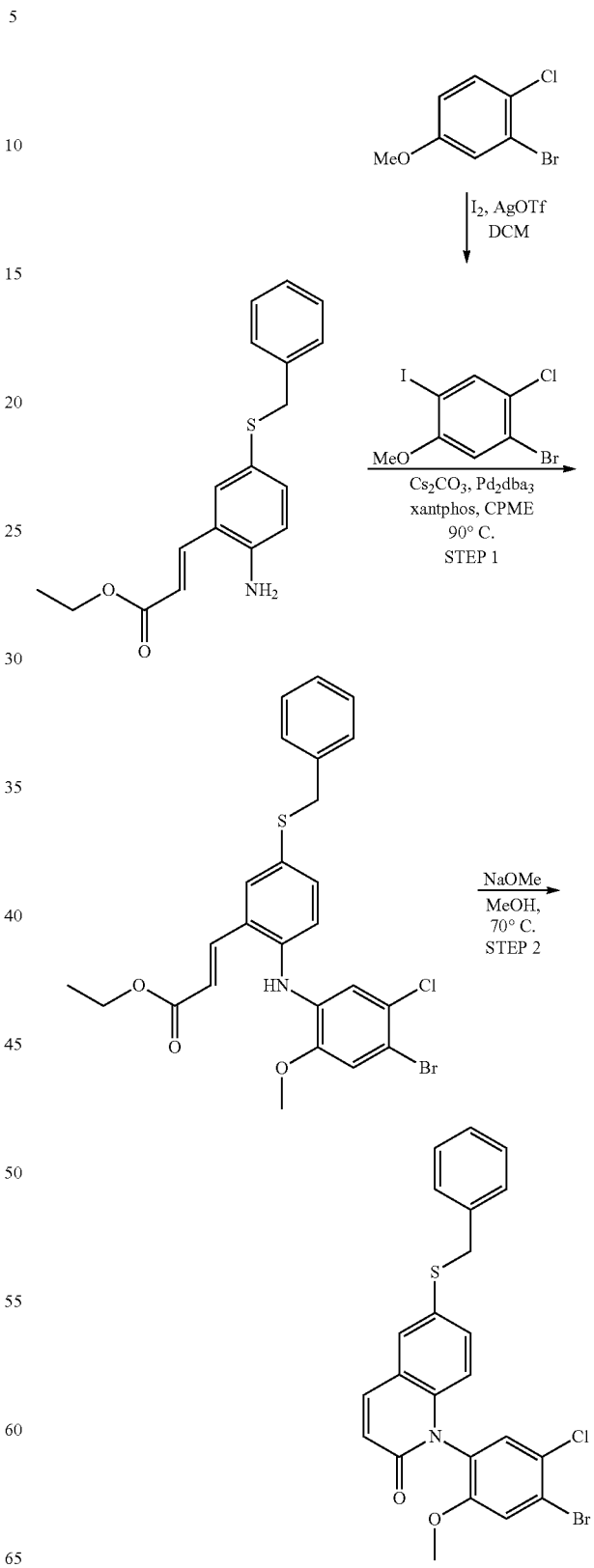

Preparation of 1-bromo-2-chloro-4-iodo-5-methoxybenzene

To a solution of 2-bromo-1-chloro-4-methoxybenzene (176.0 g, 7946 mmol, 1.0 equiv, Aurum pharmatech) in DCM (2.0 L) was added silver trifluoromethane sulfonate (224.6 g, 8641 mmol, 1.1 equiv, Angene) and the reaction mixture was stirred for 20 mins. Iodine (221.0 g, 8641 mmol, 1.1 equiv) was added to the reaction and the mixture was stirred at room temperature for 16h. The mixture was diluted with DCM (2.0 L) and filtered through celite. The celite bed was washed with DCM (2×1.0 L). The filtrate was washed with 20% aqueous sodium thiosulfate (3.0 L) and saturated aqueous sodium bicarbonate solution (2.0 L). The organic layer was dried over sodium sulfate, filtered and concentrated under reduced pressure to obtain the crude material which was purified by column chromatography (silica gel; mesh size 60-120, elution 0-5% ethyl acetate and petroleum ether) to get compound-2 (200 g, 72.4%), as off-white solid. MS (ESI, positive ion) m/z: No ionization. $^1$H NMR (400 MHz, DMSO-$d_6$) δ 7.99 (s, 1H), 7.35 (s, 1H), 3.86 (s, 3H).

Step 1: (E)-ethyl 3-(5-(benzylthio)-2-((4-bromo-5-chloro-2-methoxyphenyl)amino)phenyl)acrylate A flask was charged with (E)-ethyl 3-(2-amino-5-(benzylthio)phenyl)acrylate (See Step 3 of preparation of INTERMEDIATE B1) 50.0 g, 160 mmol), 1-bromo-2-chloro-4-iodo-5-methoxybenzene 66.5 g, 191 mmol), xantphos (4.62 g, 7.98 mmol), Pd$_2$(dba)$_3$ (3.65 g, 3.99 mmol), and cesium carbonate (72.8 g, 223 mmol). A reflux condenser was attached and the reaction placed under nitrogen atmosphere. CPME (319 ml) was added and the reaction was heated at 90° C. for 36 h. The mixture was cooled to rt and partitioned between 1000 mL of EtOAc and 1000 mL of water. The layers were separated and the aqueous layer was extracted with 200 mL of EtOAc. The combined organic layers were poured through a silica plug to provide a brown solution. The solution was concentrated until about 100 mL of solvent was left, giving a heterogeneous brown sludge. Isopropanol (500 mL) was added to the solution and a yellow solid precipitated. The yellow solid was collected by vacuum filtration (rinsing with 200 mL isopropanol) to provide desired product (E)-ethyl 3-(5-(benzylthio)-2-((4-bromo-5-chloro-2-methoxyphenyl)amino)phenyl)acrylate (76.4 g, 143 mmol, 90% yield) as a yellow solid. m/z (ESI) 531.9 (M–H)$^-$.

Step 2: 6-(benzylthio)-1-(4-bromo-5-chloro-2-methoxyphenyl)quinolin-2(1H)-one A flask was charged with (E)-ethyl 3-(5-(benzylthio)-2-((4-bromo-5-chloro-2-methoxyphenyl)amino)phenyl)acrylate (73.2 g, 137 mmol) and MeOH (687 ml) to give a yellow suspension. Sodium methoxide (25 wt % in MeOH) (15.01 ml, 54.9 mmol) was added and a reflux condenser was attached. The flask was lowered into a 70 OC heating bath and stirred at 70° C. for 18 h. The mixture was cooled to rt and poured through a 3 inch silica plug to remove black particulates. The product that was crashed out on the silica plug was washed through the plug with DCM. The mother liquor was concentrated to half its volume, then IPA (500 mL) was added and the solution concentrated again. An additional 500 mL of IPA was added and a tan solid precipitated. The tan solid was collected by vacuum filtration to give 6-(benzylthio)-1-(4-bromo-5-chloro-2-methoxyphenyl)quinolin-2(1H)-one (50.34 g, 103 mmol, 75% yield) as a dark tan powdery solid. m/z (ESI) 486.0 (M+H)$^+$.

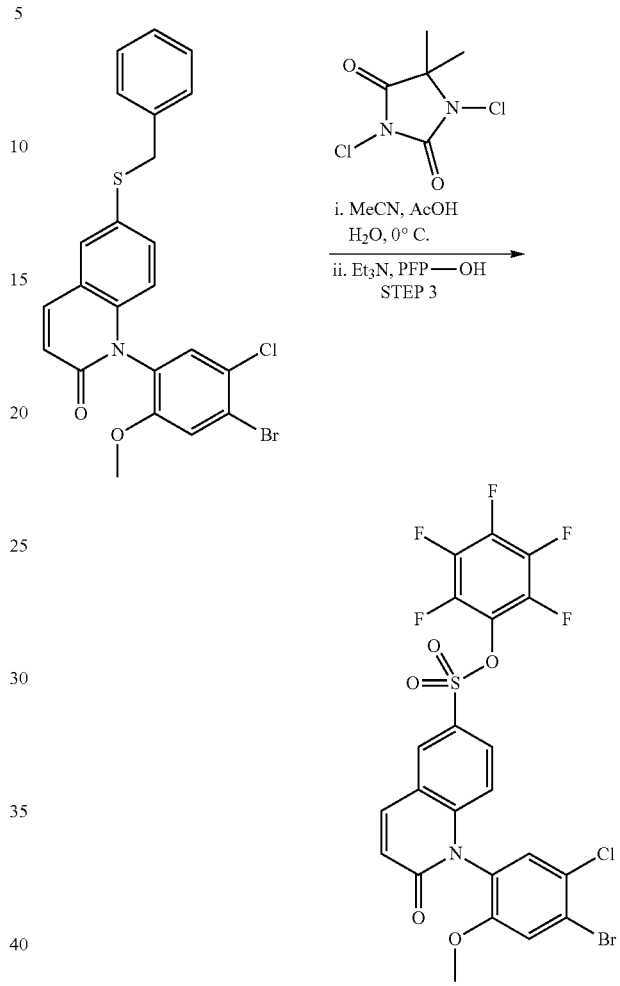

Step 3: perfluorophenyl 1-(4-bromo-5-chloro-2-methoxyphenyl)-2-oxo-1,2-dihydroquinoline-6-sulfonate A flask was charged with 6-(benzylthio)-1-(4-bromo-5-chloro-2-methoxyphenyl)quinolin-2(1H)-one (46.34 g, 95 mmol), acetonitrile (298 ml), acetic acid (11.34 ml), and water (7.46 ml). The solution was cooled to 0° C. To the solution was added 1,3-dichloro-5,5-dimethylimidazolidine-2,4-dione (18.75 g, 95 mmol) as a solid in a single portion and stirred for 10 min. An additional 0.3 equiv 1,3-dichloro-5,5-dimethylimidazolidine-2,4-dione (5.63 g, 28.6 mmol), then 0.2 eq. 1,3-dichloro-5,5-dimethylimidazolidine-2,4-dione (3.75 g, 19.04 mmol) was added until complete conversion to sulfonyl chloride 6-(benzylsulfinyl)-1-(4-bromo-5-chloro-2-methoxyphenyl)quinolin-2(1H)-one. At this time 2,3,4,5,6-pentafluorophenol (21.03 g, 114 mmol) was added as a warmed liquid (gooey solid at rt), using 10 mL of acetonitrile to aid in transfer from pre-tared vial containing the 2,3,4,5,6-pentafluorophenol. Then, TEA (53.1 ml, 381 mmol) was added from an addition funnel. During the addition, a white fume was produced. The solution was maintained at 0° C. for 30 min and then allowed to warm to rt and stir for 20 min. The reaction mixture was partitioned between 1:1 brine:water (500 mL) and EtOAc (700 mL) The layers were separated and the aqueous layer was extracted with EtOAc (2×400 mL). Both layers had suspended white solid. The combined organic layers were filtered to remove suspended solid and concentrated to give a brown sludge. The solid that was collected was clean product perfluorophenyl 1-(4-bromo-5-chloro-2-methoxyphenyl)-2-oxo-1,2-dihydroquinoline-6-sulfonate which was set aside. The remaining brown sludge was taken up in IPA (500 mL) and a tan solid precipitated, which was collected by vacuum filtration (rinsing with 200 mL IPA) to give an additional 19.961 g perfluorophenyl 1-(4-bromo-5-chloro-2-methoxyphenyl)-2-oxo-1,2-dihydroquinoline-6-sulfonate. The aqueous layer still had tan suspended solid, which was extracted with DCM (2×500 mL). The combined organic layers were concentrated to give 4.542 g perfluorophenyl 1-(4-bromo-5-chloro-2-methoxyphenyl)-2-oxo-1,2-dihydroquinoline-6-sulfonate as a tan solid. The three lots were combined to give 36.21 g, 59.3 mmol (62.3% yield) of perfluorophenyl 1-(4-bromo-5-chloro-2-methoxyphenyl)-2-oxo-1,2-dihydroquinoline-6-sulfonate. $^1$H NMR (400 MHz, DMSO-$d_6$) δ 8.60 (d, J=2.35 Hz, 1H), 8.19-8.31 (m, 1H), 7.96 (dd, J=2.30, 9.05 Hz, 1H), 7.82-7.89 (m, 1H), 7.74-7.80 (m, 1H), 6.92-6.98 (m, 1H), 6.84-6.91 (m, 1H), 3.71-3.80 (s, 3H). m/z (ESI) 609.9 (M+H)$^+$.

Step 4: (P)-perfluorophenyl 1-(4-bromo-5-chloro-2-methoxyphenyl)-2-oxo-1,2-dihydroquinoline-6-sulfonate Racemic perfluorophenyl 1-(4-bromo-5-chloro-2-methoxyphenyl)-2-oxo-1,2-dihydroquinoline-6-sulfonate (36.21 g) was separated by chiral SFC via (S,S) Whelk-O column (5 micron, 5×15 cm) eluting with 50% isopropanol/50% $CO_2$ to give (P)-perfluorophenyl 1-(4-bromo-5-chloro-2-methoxyphenyl)-2-oxo-1,2-dihydroquinoline-6-sulfonate and (M)-perfluorophenyl 1-(4-bromo-5-chloro-2-methoxyphenyl)-2-oxo-1,2-dihydroquinoline-6-sulfonate. Data for peak 1: m/z (ESI) 609.9 (M+H)$^+$. Data for peak 2: m/z (ESI) 609.9 (M+H)$^+$.

Intermediate B4: (P)-perfluorophenyl 1-(4-bromo-2-methoxyphenyl)-2-oxo-1,2-dihydroquinoline-6-sulfonate

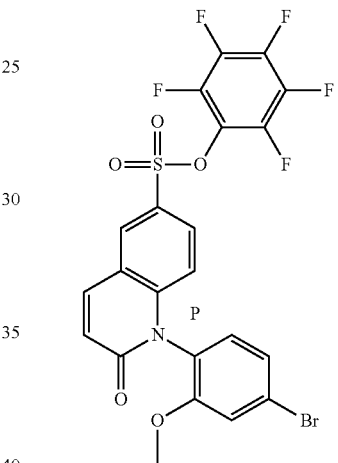

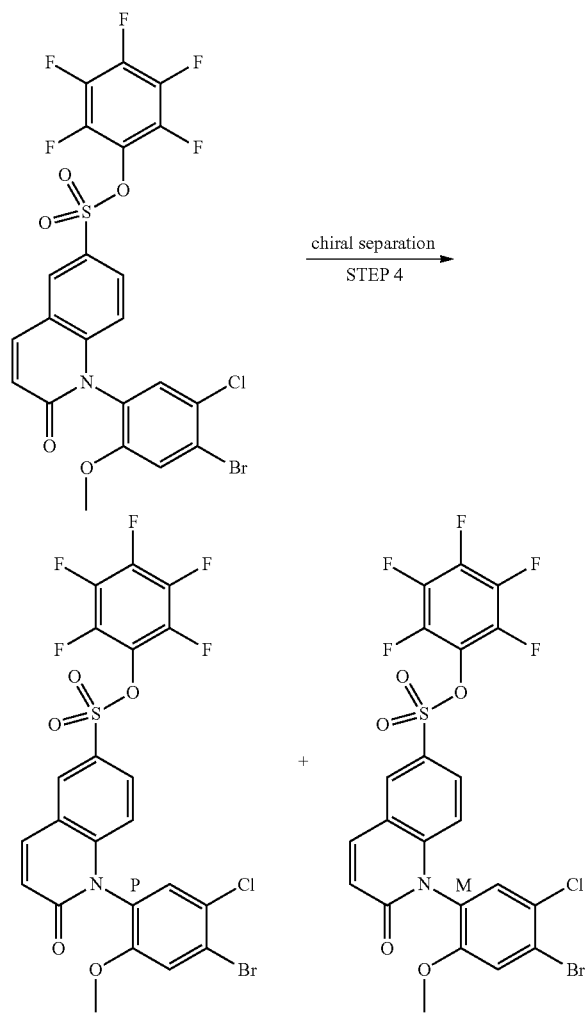

(P)-Perfluorophenyl 1-(4-bromo-2-methoxyphenyl)-2-oxo-1,2-dihydroquinoline-6-sulfonate was synthesized in a manner similar to that described for INTERMEDIATE B3 above, except using 5-bromo-2-iodoanisole (Purchased from Oakwood) instead of 1-bromo-2-chloro-4-iodo-5-methoxybenzene in Step 1. The resulting racemic perfluorophenyl 1-(4-bromo-2-methoxyphenyl)-2-oxo-1,2-dihydroquinoline-6-sulfonate was separated by chiral SFC via (S,S) Whelk-O column (5 micron, 5×15 cm) eluting with 50% isopropanol/50% $CO_2$ to give (P)-perfluorophenyl 1-(4-bromo-2-methoxyphenyl)-2-oxo-1,2-dihydroquinoline-6-sulfonate and (M)-perfluorophenyl 1-(4-bromo-2-methoxyphenyl)-2-oxo-1,2-dihydroquinoline-6-sulfonate. Data for peak 1: m/z (ESI) 575.9 (M+H)$^+$. Data for peak 2: m/z (ESI) 575.9 (M+H)$^+$.

EXAMPLES

Example 1 (P)-1-(4-((4,4-difluorocyclohexyl)ethynyl)-5-fluoro-2-methoxyphenyl)-N-(isoxazol-3-yl)-2-oxo-1,2-dihydroquinoline-6-sulfonamide

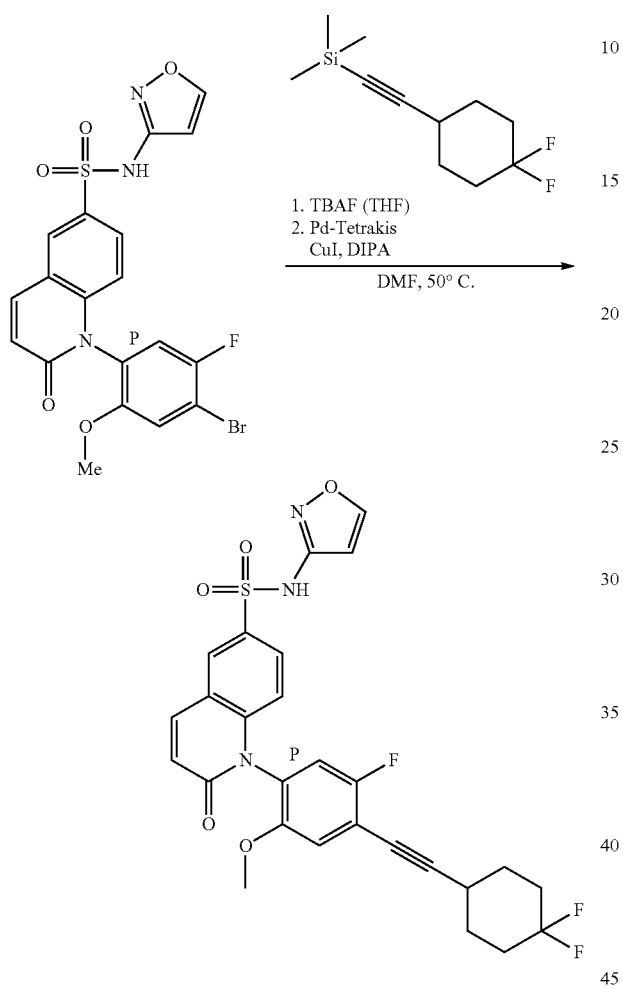

To a mixture of (((4,4-difluorocyclohexyl)ethynyl)trimethylsilane (See INTERMEDIATE A3 above, 0.744 g, 3.44 mmol) in 5 mL of THF, was added TBAF (1M in THF) (3.44 mL, 3.44 mmol). The resulting mixture was stirred at ambient temperature for 15 minutes. The reaction was diluted with DMF (10 mL) and to this was added (P)-1-(4-bromo-5-fluoro-2-methoxyphenyl)-N-(isoxazol-3-yl)-2-oxo-1,2-dihydroquinoline-6-sulfonamide (See INTERMEDIATE B2 above, 1 g, 2.023 mmol), Pd-tetrakis (0.468 g, 0.405 mmol), copper(I) iodide (0.077 g, 0.405 mmol) and diisopropylamine (4.33 mL, 30.3 mmol). The reaction was purged with nitrogen and then stirred at 50° C. for 5 hours. The mixture was cooled to ambient temperature and poured slowly into a chilled 1:1 mixture of 1N aqueous HCl and ethyl acetate (100 mL). The organic portion was collected, dried over sodium sulfate and concentrated. The resulting crude was purified in 10-60% (EtOA/EtOH 3:1 blend)/Heptane to give (P) 1-(4-((4,4-difluorocyclohexyl)ethynyl)-5-fluoro-2-methoxyphenyl)-N-(isoxazol-3-yl)-2-oxo-1,2-dihydroquinoline-6-sulfonamide (800 mg, 1.435 mmol, 70.9% yield) as a white solid. MS m/z=558 (M+H). $^1$H NMR (400 MHz, DMSO-$d_6$) δ ppm 11.65 (br. s, 1H) 8.71-8.75 (m, 1H) 8.36 (d, J=2.18 Hz, 1H) 8.21 (d, J=9.59 Hz, 1H) 7.82 (dd, J=8.97, 2.23 Hz, 1H) 7.48 (d, J=9.23 Hz, 1H) 7.37 (d, J=6.32 Hz, 1H) 6.76-6.81 (m, 2H) 6.40-6.45 (m, 1H) 3.67 (s, 3H) 2.86-3.06 (m, 1H) 1.81-2.12 (m, 8H).

Example 2 (P)-1-(5-fluoro-2-methoxy-4-(4,4,4-trifluoro-3,3-dimethylbut-1-yn-1-yl)phenyl)-N-(isoxazol-3-yl)-2-oxo-1,2-dihydroquinoline-6-sulfonamide

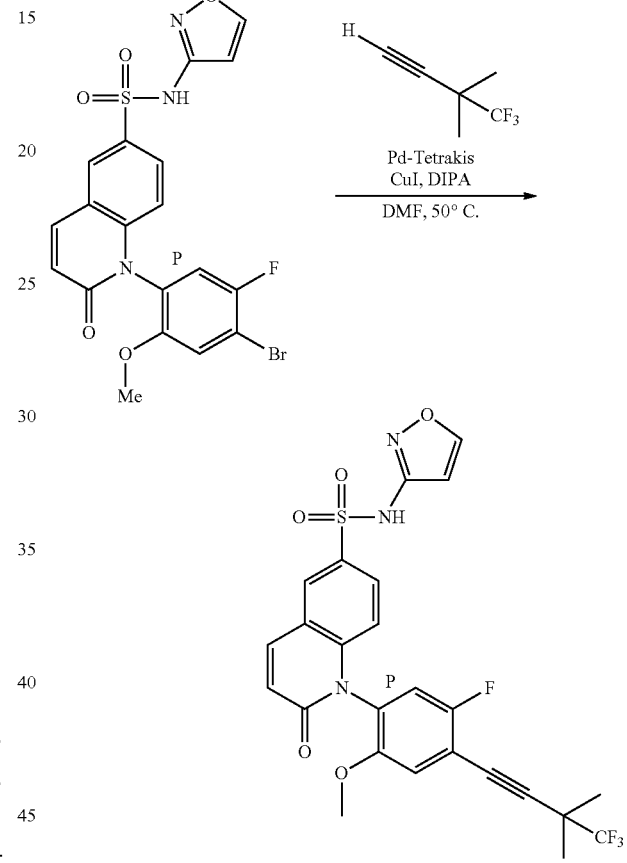

To a solution of (P)-1-(4-bromo-5-fluoro-2-methoxyphenyl)-N-(isoxazol-3-yl)-2-oxo-1,2-dihydroquinoline-6-sulfonamide (See INTERMEDIATE B2 above, 0.25 g, 0.46 mmol) in DMF (2 mL) was added 4,4,4-trifluoro-3,3-dimethylbut-1-yne (See INTERMEDIATE A2 above, 0.16 g, 1.14 mmol), copper(I) iodide (0.013 g, 0.068 mmol), Pd-tetrakis (0.079 g, 0.068 mmol) and diisopropylamine (0.649 mL, 4.55 mmol). The reaction was purged with nitrogen and then stirred at 50° C. for 16 hours. The mixture was cooled to ambient temperature and then treated slowly with 1N aqueous HCl and EtOAc. The organic portion was concentrated and purified in 10-80% {EtOAc/EtOH blend (3:1)} in Heptanes to give (P)-1-(5-fluoro-2-methoxy-4-(4,4,4-trifluoro-3,3-dimethylbut-1-yn-1-yl)phenyl)-N-(isoxazol-3-yl)-2-oxo-1,2-dihydroquinoline-6-sulfonamide (50 mg, 0.092 mmol, 20% yield) as an off-white solid. MS m/z=550 (M+H). $^1$H NMR (400 MHz, DMSO-$d_6$) δ ppm 11.66 (br. s, 1H) 8.71-8.74 (m, 1H) 8.37 (d, J=2.13 Hz, 1H) 8.22 (d, J=9.69 Hz, 1H) 7.82 (dd, J=8.97, 2.23 Hz, 1H) 7.54 (d, J=9.17 Hz, 1H) 7.39 (d, J=6.22 Hz, 1H) 6.78-6.85 (m, 2H) 6.43-6.45 (m, 1H) 3.71 (s, 3H) 1.57 (s, 6H).

Example 3 (P)-1-(4-(cyclopentylethynyl)-2-methoxyphenyl)-N-(isoxazol-3-yl)-2-oxo-1,2-dihydroquinoline-6-sulfonamide

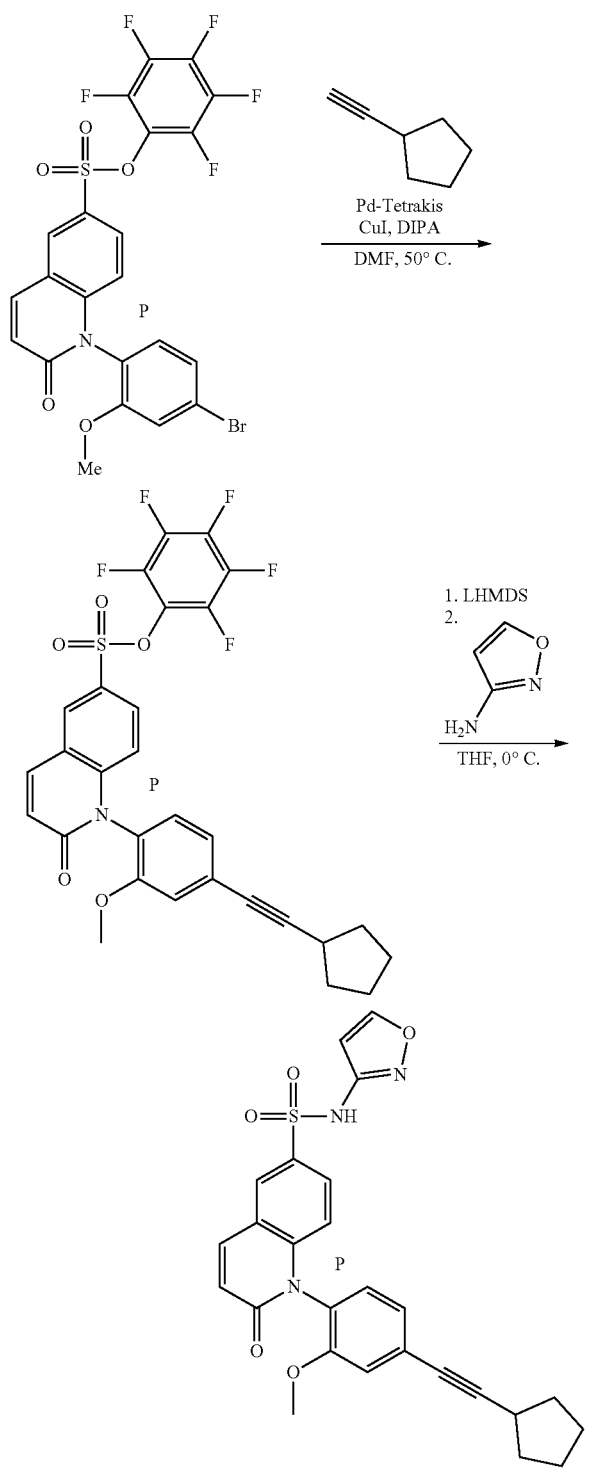

Step 1: (P)-perfluorophenyl 1-(4-(cyclopentylethynyl)-2-methoxyphenyl)-2-oxo-12-dihydroquinoline-6-sulfonate To a solution of (P)-perfluorophenyl 1-(4-bromo-2-methoxyphenyl)-2-oxo-1,2-dihydroquinoline-6-sulfonate (See intermediate B4, 1.4 g, 2.429 mmol) in DMF (12 mL) was added ethynylcyclopentane (Aldrich)? 1.144 g, 12.15 mmol), copper(i) iodide (10.70 µl, 0.316 mmol), Pd-tetrakis (0.281 g, 0.243 mmol), and diisopropylamine (1.731 mL, 12.15 mmol). The resulting mixture was stirred at 50° C. for 3 hours. The mixture was cooled to ambient temperature and then treated slowly with 1N aqueous HCl solution and EtOAc and stirred for 10 minutes. The organic portion was collected, dried over sodium sulfate and concentrated to half its volume. Upon cooling of the organic portion, an off-white precipitate formed. This was collected and dried to give (P)-perfluorophenyl 1-(4-(cyclopentylethynyl)-2-methoxyphenyl)-2-oxo-1,2-dihydroquinoline-6-sulfonate (0.8 g, 1.36 mmol, 55.9% yield). MS m/z=590 (M+H).

Step 2: (P)-1-(4-(cyclopentylethynyl)-2-methoxyphenyl)-N-(isoxazol-3-yl)-2-oxo-1,2-dihydroquinoline-6-sulfonamide A mixture of (P)-perfluorophenyl 1-(4-(cyclopentylethynyl)-2-methoxyphenyl)-2-oxo-1,2-dihydroquinoline-6-sulfonate (284 mg, 0.409 mmol) and isoxazol-3-amine (51.6 mg, 0.614 mmol) in tetrahydrofuran (3 mL) was placed in an ice bath and allowed to cool for 15 minutes. LHMDS (1M in THF) (0.90 mL, 0.901 mmol) was then added dropwise via syringe. The mixture was stirred for an additional 15 minutes. The reaction was slowly acidified with 1N aqueous HCl (50 mL) and then extracted with ethyl acetate. The organic portion was washed with brine and then concentrated to afford a yellow residue. This was purified in 10-80% {EtOAc/EtOH blend (3:1)} in Heptanes to give (P)-1-(4-(cyclopentylethynyl)-2-methoxyphenyl)-N-(isoxazol-3-yl)-2-oxo-1,2-dihydroquinoline-6-sulfonamide (80 mg, 0.163 mmol, 39.9% yield) as a light yellow solid. MS m/z=490 (M+H). $^1$H NMR (400 MHz, DMSO-$d_6$) δ ppm 11.59 (br. s, 1H) 8.64-8.68 (m, 1H) 8.30 (d, J=2.23 Hz, 1H) 8.15 (d, J=9.64 Hz, 1H) 7.77 (dd, J=8.99, 2.20 Hz, 1H) 7.17-7.25 (m, 2H) 7.05-7.12 (m, 1H) 6.64-6.77 (m, 2H) 6.38-6.40 (m, 1H) 3.62 (s, 3H) 2.82-2.90 (m, 1H) 1.91-1.99 (m, 2H) 1.51-1.73 (m, 6H).

Example 4 (P)-1-(5-fluoro-2-methoxy-4-((2-(trifluoromethyl)cyclopropyl)ethynyl)phenyl)-N-(isoxazol-3-yl)-2-oxo-1,2-dihydroquinoline-6-sulfonamide

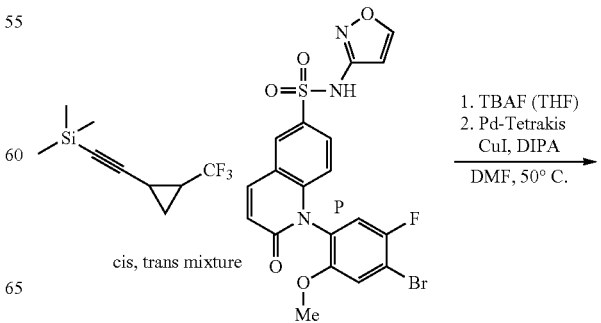

-continued

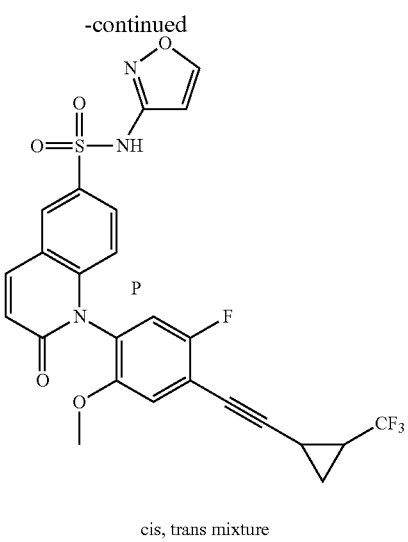

cis, trans mixture

Step 1: Preparation of the Title Compound

The title compound was prepared in an analogous manner to that of (P)-1-(4-((4,4-difluorocyclohexyl)ethynyl)-5-fluoro-2-methoxyphenyl)-N-(isoxazol-3-yl)-2-oxo-1,2-dihydroquinoline-6-sulfonamide of Example 1, except that trimethyl((2-(trifluoromethyl)cyclopropyl)ethynyl)silane (INTERMEDIATE A3) was used instead of ((4,4-difluorocyclohexyl)ethynyl)trimethylsilane (INTERMEDIATE A4). MS m/z=548 (M+H). $^1$H NMR (400 MHz, DMSO-$d_6$) δ ppm 11.61 (br. s, 1H) 8.66-8.69 (m, 1H) 8.32 (d, J=2.18 Hz, 1H) 8.17 (d, J=9.69 Hz, 1H) 7.79 (dd, J=8.99, 2.20 Hz, 1H) 7.45 (d, J=9.23 Hz, 1H) 7.35 (d, J=6.32 Hz, 1H) 6.71-6.77 (m, 2H) 6.38-6.41 (m, 1H) 3.62 (s, 3H) 2.22-2.31 (m, 1H) 1.32-1.41 (m, 2H) 1.14-1.18 (m, 1H)

Step 2: Separation of Cis and Trans Isomers to Examples 4A and 4B:

The cis and trans mixture was then separated via supercritical fluid chromatography (SFC). The column used was Chiralpak OJ-H. The mobile phase was run under isocratic conditions; $CO_2$ with 15% Methanol to afford:

Example 4A (P)-1-(4-((4,4-difluorocyclohexyl)ethynyl)-5-fluoro-2-methoxyphenyl)-N-(isoxazol-3-yl)-2-oxo-1,2-dihydroquinoline-6-sulfonamide (arbitrarily assigned as the cis cyclopropyl isomer, racemic). MS m/z=548 (M+H). $^1$H NMR (400 MHz, DMSO-$d_6$) δ ppm 11.61 (br. s, 1H) 8.66-8.69 (m, 1H) 8.32 (d, J=2.18 Hz, 1H) 8.17 (d, J=9.69 Hz, 1H) 7.79 (dd, J=8.99, 2.20 Hz, 1H) 7.45 (d, J=9.23 Hz, 1H) 7.35 (d, J=6.32 Hz, 1H) 6.71-6.77 (m, 2H) 6.38-6.41 (m, 1H) 3.62 (s, 3H) 2.26-2.32 (m, 1H) 1.39-1.46 (m, 2H) 1.05-1.11 (m, 1H) and Example 4B (P)-1-(4-((4,4-difluorocyclohexyl)ethynyl)-5-fluoro-2-methoxyphenyl)-N-(isoxazol-3-yl)-2-oxo-1,2-dihydroquinoline-6-sulfonamide (arbitrarily assigned as the trans cyclopropyl isomer, racemic). MS m/z=548 (M+H). $^1$H NMR (400 MHz, DMSO-$d_6$) δ ppm 11.61 (br. s, 1H) 8.66-8.69 (m, 1H) 8.32 (d, J=2.18 Hz, 1H) 8.17 (d, J=9.69 Hz, 1H) 7.79 (dd, J=8.99, 2.20 Hz, 1H) 7.45 (d, J=9.23 Hz, 1H) 7.35 (d, J=6.32 Hz, 1H) 6.71-6.77 (m, 2H) 6.38-6.41 (m, 1H) 3.62 (s, 3H) 2.24-2.28 (m, 1H) 1.35-1.43 (m, 2H) 1.11-1.13 (m, 1H).

Example 5: (P)-1-(5-fluoro-2-methoxy-4-((1-(trifluoromethyl)cyclopropyl)ethynyl)phenyl)-N-(isoxazol-3-yl)-2-oxo-1,2-dihydroquinoline-6-sulfonamide

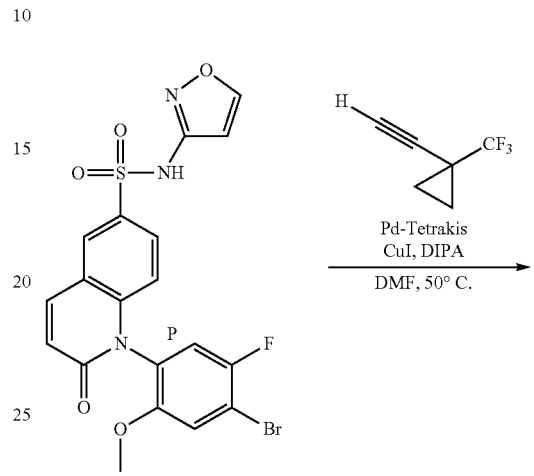

The title compound was prepared in an analogous manner to that of (P)-1-(5-fluoro-2-methoxy-4-(4,4,4-trifluoro-3,3-dimethylbut-1-yn-1-yl)phenyl)-N-(isoxazol-3-yl)-2-oxo-1,2-dihydroquinoline-6-sulfonamide of Example 2, except that 1-ethynyl-1-(trifluoromethyl)cyclopropane (INTERMEDIATE A1) was used instead of 4,4,4-trifluoro-3,3-dimethylbut-1-yne. MS m/z=548 (M+H). $^1$H NMR (400 MHz, DMSO-$d_6$) δ ppm 11.67 (br. s, 1H) 8.71-8.74 (m, 1H) 8.37 (d, J=2.18 Hz, 1H) 8.23 (d, J=9.64 Hz, 1H) 7.83 (dd, J=8.97, 2.23 Hz, 1H) 7.54 (d, J=9.17 Hz, 1H) 7.42 (d, J=6.22 Hz, 1H) 6.76-6.84 (m, 2H) 6.41-6.47 (m, 1H) 3.68 (s, 3H) 1.51-1.56 (m, 2H) 1.43-1.48 (m, 2H).

Example 6: (P)-1-(5-chloro-4-(cyclopentylethynyl)-2-methoxyphenyl)-N-(isoxazol-3-yl)-2-oxo-1,2-dihydroquinoline-6-sulfonamide

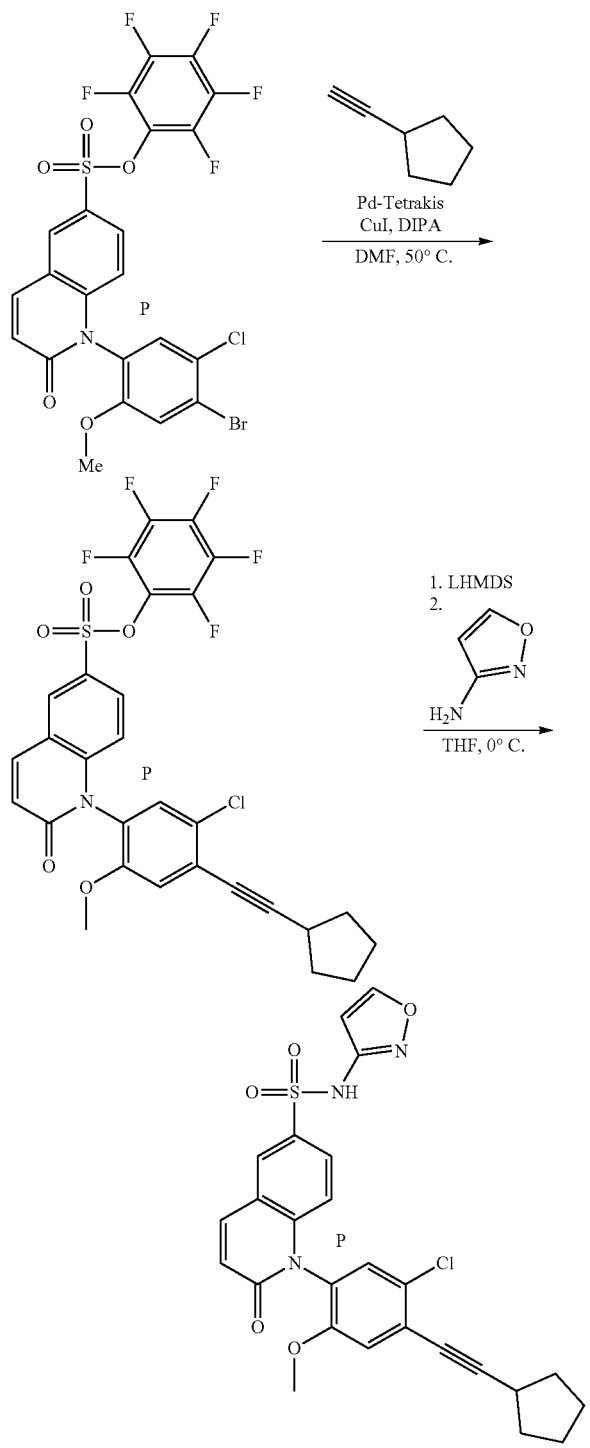

The title compound was prepared in an analogous manner to that of (P)-1-(4-(cyclopentylethynyl)-2-methoxyphenyl)-N-(isoxazol-3-yl)-2-oxo-1,2-dihydroquinoline-6-sulfonamide of Example 3, except that (P)-perfluorophenyl 1-(4-bromo-5-chloro-2-methoxyphenyl)-2-oxo-1,2-dihydroquinoline-6-sulfonate (INTERMEDIATE B3) was used instead of (P)-perfluorophenyl 1-(4-bromo-2-methoxyphenyl)-2-oxo-1,2-dihydroquinoline-6-sulfonate (INTERMEDIATE B4) in step 1. MS m/z=524 (M+H). $^1$H NMR (500 MHz, DMSO-$d_6$) δ ppm 11.67 (br. s, 1H) 8.71-8.74 (m, 1H) 8.31-8.35 (m, 1H) 8.20 (d, J=9.67 Hz, 1H) 7.83 (dd, J=8.92, 2.04 Hz, 1H) 7.61 (s, 1H) 7.38 (s, 1H) 6.76-6.82 (m, 2H) 6.41-6.44 (m, 1H) 3.68 (s, 3H) 2.98-3.01 (m, 1H) 2.01-2.04 (m, 2H) 1.71-1.82 (m, 6H).

Example 7: (P) 1-(4-((3,3-difluorocyclohexyl)ethynyl)-5-fluoro-2-methoxyphenyl)-N-(isoxazol-3-yl)-2-oxo-1,2-dihydroquinoline-6-sulfonamide

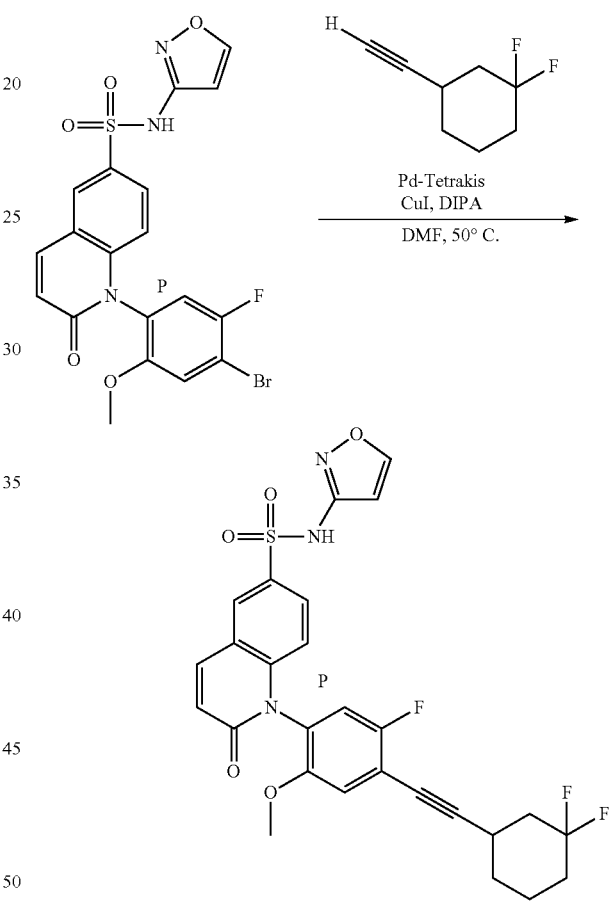

The title compound was prepared in an analogous manner to that of (P)-1-(5-fluoro-2-methoxy-4-(4,4,4-trifluoro-3,3-dimethylbut-1-yn-1-yl)phenyl)-N-(isoxazol-3-yl)-2-oxo-1,2-dihydroquinoline-6-sulfonamide of Example 2, except that 3-ethynyl-1,1-difluorocyclohexane (INTERMEDIATE A5) was used instead of 4,4,4-trifluoro-3,3-dimethylbut-1-yne. MS m/z=558 (M+H). $^1$H NMR (400 MHz, DMSO-$d_6$) δ ppm 11.66 (br. s, 1H) 8.71-8.74 (m, 1H) 8.31-8.35 (m, 1H) 8.22 (d, J=9.64 Hz, 1H) 7.83 (dd, J=8.97, 2.23 Hz, 1H) 7.48 (d, J=9.23 Hz, 1H) 7.34 (d, J=6.32 Hz, 1H) 6.74-6.82 (m, 2H) 6.41-6.44 (m, 1H) 3.67 (s, 3H) 2.90-3.02 (m, 1H) 1.81-2.06 (m, 6H) 1.53-1.61 (m, 2H).

Example 8: (P)-1-(5-fluoro-2-methoxy-4-((1-(2,2,2-trifluoroethoxy)cyclopentyl)ethynyl)phenyl)-N-(isoxazol-3-yl)-2-oxo-1,2-dihydroquinoline-6-sulfonamide

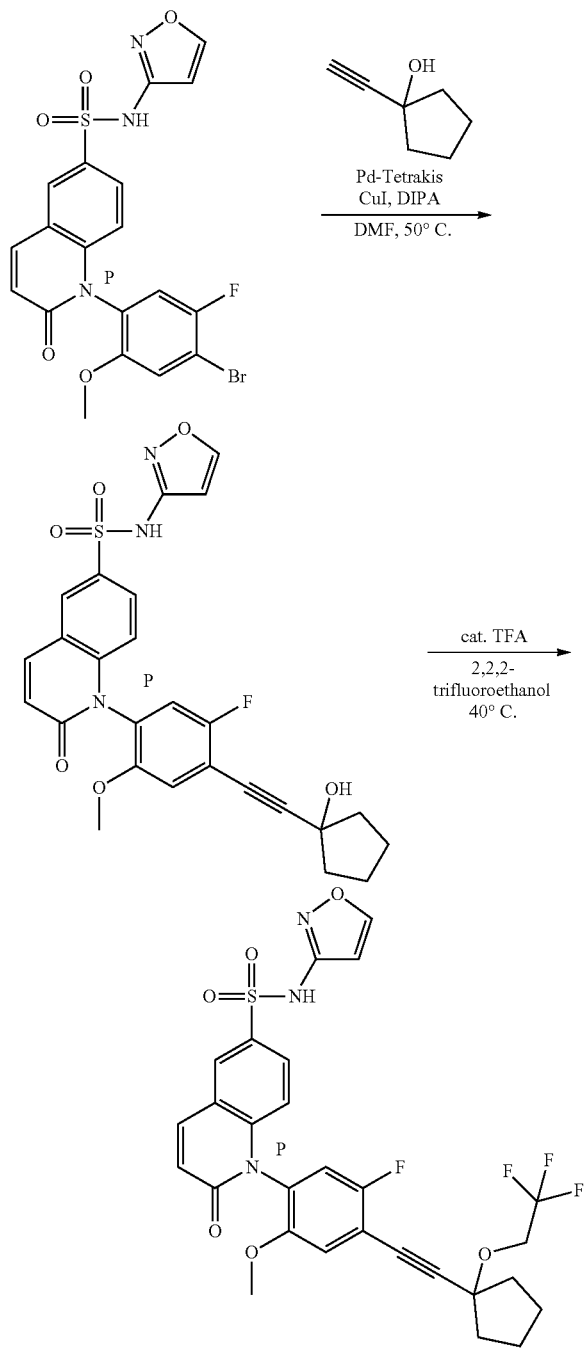

Step 1: (P)-1-(5-fluoro-4-((1-hydroxycyclopentyl)ethynyl)-2-methoxyphenyl)-N-(isoxazol-3-yl)-2-oxo-1,2-dihydroquinoline-6-sulfonamide To a mixture of (P)-1-(4-bromo-5-fluoro-2-methoxyphenyl)-N-(isoxazol-3-yl)-2-oxo-1,2-dihydroquinoline-6-sulfonamide (See INTERMEDIATE B2 above, 1.15 g, 2.327 mmol) in DMF (12 mL) was added 1-ethynylcyclopentanol (Aldrich) 0.799 mL, 6.98 mmol), copper(i) iodide (0.012 mL, 0.349 mmol), Pd-tetrakis (0.403 g, 0.349 mmol) and diisopropylamine (3.32 mL, 23.27 mmol). The resulting mixture was stirred at 50° C. for 3 hours. The mixture was cooled to ambient temperature and then treated slowly with 1N aqueous HCl solution and EtOAc and stirred for 10 minutes. The organic portion was collected, dried over sodium sulfate and concentrated to give a brown residue. This was purified in 10-80% {EtOAc/EtOH blend (3:1)} in Heptanes to give (P)-1-(5-fluoro-4-((1-hydroxycyclopentyl)ethynyl)-2-methoxyphenyl)-N-(isoxazol-3-yl)-2-oxo-1,2-dihydroquinoline-6-sulfonamide (1.0 g, 1.91 mmol, 82% yield) as a tan solid. MS m/z=524 (M+H).

Step 2: (P)-1-(5-fluoro-2-methoxy-4-((1-(2,2,2-trifluoroethoxy)cyclopentyl)ethynyl)phenyl)-N-(isoxazol-3-yl)-2-oxo-1, 2-dihydroquinoline-6-sulfonamide A mixture of (P)-1-(5-fluoro-4-((1-hydroxycyclopentyl)ethynyl)-2-methoxyphenyl)-N-(isoxazol-3-yl)-2-oxo-1,2-dihydroquinoline-6-sulfonamide (80 mg, 0.153 mmol) and trifluoroacetic acid (1.177 µl, 0.015 mmol) in 2,2,2-trifluoroethanol (509 µl) was stirred at 40° C. for 16 hours. The mixture was cooled to ambient temperature and then diluted with DCM and water. The organic portion was collected, dried over sodium sulfate and concentrated to afford a yellow residue. This was purified via reverse phase (20-70% CH3CN/Water; TFA modifier) to give (P)-1-(5-fluoro-2-methoxy-4-((1-(2,2,2-trifluoroethoxy)cyclopentyl)ethynyl)phenyl)-N-(isoxazol-3-yl)-2-oxo-1,2-dihydroquinoline-6-sulfonamide (36 mg, 0.059 mmol, 38.9% yield) as a white solid. MS m/z=606 (M+H). $^1$H NMR (400 MHz, DMSO-$d_6$) δ ppm 11.66 (br. s, 1H) 8.71-8.75 (m, 1H) 8.34-8.38 (m, 1H) 8.23 (d, J=9.64 Hz, 1H) 7.83 (dd, J=8.97, 2.23 Hz, 1H) 7.54 (d, J=9.12 Hz, 1H) 7.45 (d, J=6.22 Hz, 1H) 6.79-6.86 (m, 2H) 6.46 (d, J=1.81 Hz, 1H) 4.21 (q, J=9.21 Hz, 2H) 3.69 (s, 3H) 2.14-2.22 (m, 2H) 2.01-2.08 (m, 2H) 1.73-1.82 (m, 4H).

Example 9: (P)-1-(4-(cyclopentylethynyl)-5-fluoro-2-methoxyphenyl)-2-oxo-N-3-pyridazinyl-1,2-dihydro-6-quinoline sulfonamide

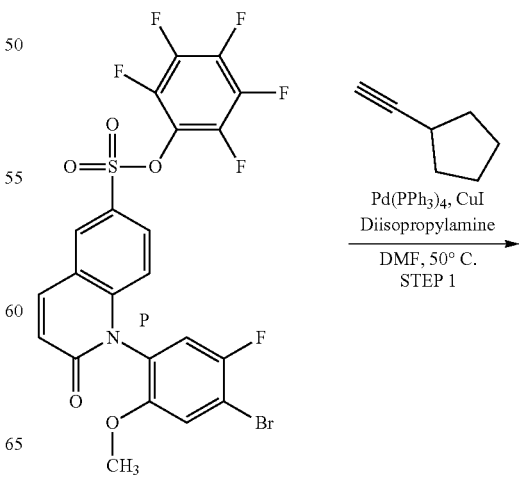

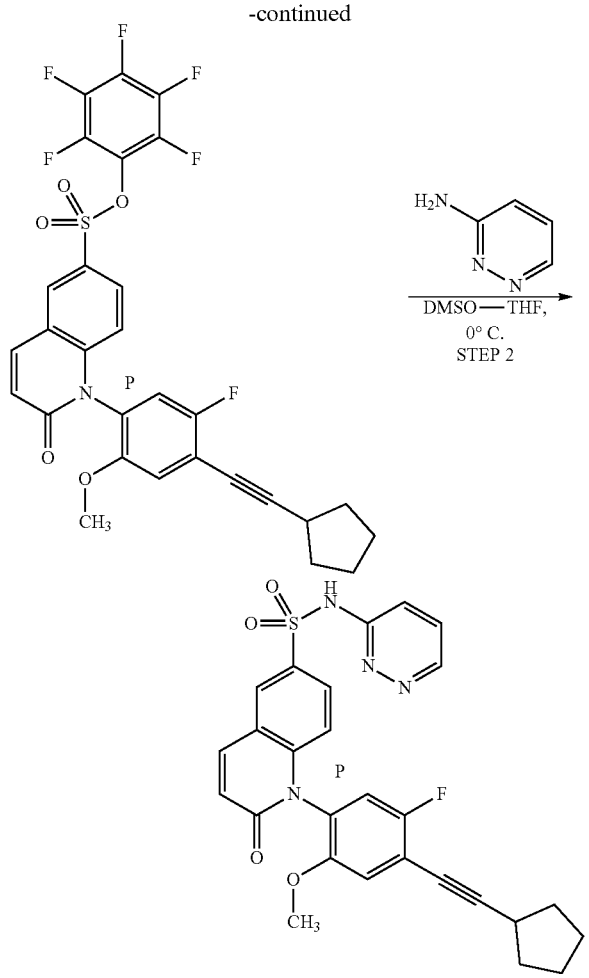

Step 1: (P)-perfluorophenyl 1-(4-(cyclopentylethynyl)-5-fluoro-2-methoxyphenyl)-2-oxo-1,2-dihydroquinoline-6-sulfonate A round bottomed flask was charged with (P)-perfluorophenyl 1-(4-bromo-5-fluoro-2-methoxyphenyl)-2-oxo-1,2-dihydroquinoline-6-sulfonate (See Step 1 of INTERMEDIATE B2 above, 2 g, 3.37 mmol), ethynylcyclopentane (Aldrich) 1.584 g, 16.83 mmol), diisopropylamine (2.398 ml, 16.83 mmol), copper(i) iodide (0.064 g, 0.337 mmol), Tetrakis(triphenylphosphine)palladium(0) (0.389 g, 0.337 mmol), and DMF (16.83 ml). The reaction was stirred at 50° C. for 3 hrs. The mixture was diluted with water and Ethyl Acetate. The organic portion was collected, dried with sodium sulfate, filtered, and concentrated. The crude material was purified via column chromatography (RediSep Gold 40 g, gradient elution 10-75% [3:1 EtOAc/EtOH]:Heptane to give (P)-perfluorophenyl 1-(4-(cyclopentylethynyl)-5-fluoro-2-methoxyphenyl)-2-oxo-1,2-dihydroquinoline-6-sulfonate (1.25 g, 2.058 mmol, 61.1% yield) as an off-white solid. m/z (ESI) 608.0 (M+H)$^+$.

Step 2: (P)-1-(4-(cyclopentylethynyl)-5-fluoro-2-methoxyphenyl)-2-oxo-N-3-pyridazinyl-1,2-dihydro-6-quinoline sulfonamide A round bottomed flask was charged with (P)-perfluorophenyl 1-(4-(cyclopentylethynyl)-5-fluoro-2-methoxyphenyl)-2-oxo-1,2-dihydroquinoline-6-sulfonate (179 mg, 0.295 mmol) and pyridazin-3-amine (36.4 mg, 0.383 mmol). DMSO (0.76 ml) was added to give a solution which was then diluted with THF (2.21 ml). The flask was cooled in an ice-water bath for 15 mins, then lithium bis(trimethylsilyl)amide (1M in THF) (678 μl, 0.678 mmol) was added dropwise, slowly over 2 min. After 15 min, the mixture was diluted with 1N aq. HCl and EtOAc. The layers were separated, and the aq. layer was extracted with EtOAc (2×). The combined organic extracts were dried over sodium sulfate, filtered, and concentrated. The residue was purified by chromatography on silica gel (50-g SNAP Ultra column, 10-70% of a 3:1 EtOAc/EtOH solution in heptane with 10% DCM as additive). Fractions containing pure product were combined and concentrated to give (P)-1-(4-(cyclopentylethynyl)-5-fluoro-2-methoxyphenyl)-2-oxo-N-(pyridazin-3-yl)-1,2-dihydroquinoline-6-sulfonamide (60 mg, 0.116 mmol, 39.3% yield) as an off-white solid. $^1$H NMR (400 MHz, DMSO-d$_6$) δ ppm 14.46 (br. s., 1H) 8.25-8.38 (m, 2H) 8.19 (d, J=9.64 Hz, 1H) 7.90-7.97 (m, 1H) 7.82 (dd, J=8.81, 1.76 Hz, 1H) 7.69 (dd, J=9.54, 4.25 Hz, 1H) 7.43 (d, J=9.23 Hz, 1H) 7.32 (d, J=6.43 Hz, 1H) 6.70-6.77 (m, 2H) 3.66 (s, 3H) 2.95-3.01 (m, 1H) 1.98-2.08 (m, 2H) 1.58-1.79 (m, 6H). m/z (ESI) 519.0 (M+H)$^+$.

Example 10: (P)-1-(4-(cyclopentylethynyl)-5-fluoro-2-methoxyphenyl)-N-3-isoxazolyl-2-oxo-1,2-dihydro-6-quinoline Sulfonamide

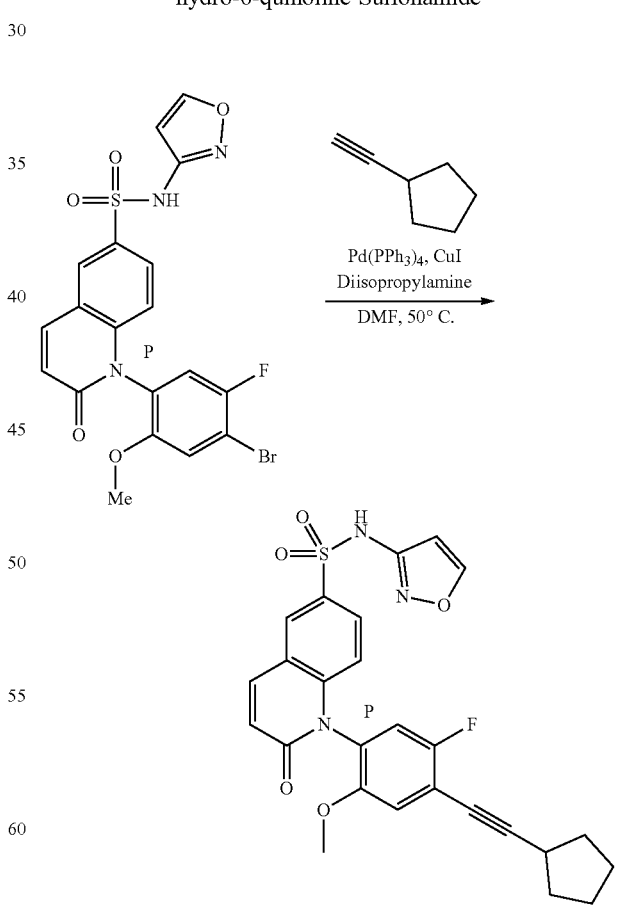

A round bottomed flask was charged with (P)-1-(4-bromo-5-fluoro-2-methoxyphenyl)-N-(isoxazol-3-yl)-2-oxo-1,2-dihydroquinoline-6-sulfonamide (See INTERME- DIATE B2 above, 234 mg, 0.272 mmol), Tetrakis(triphenylphosphine)palladium(0) (31.5 mg, 0.027 mmol), copper(i) iodide (1.384 μl, 0.041 mmol), diisopropylamine (582 μl, 4.08 mmol), 3,3-dimethylbut-1-yne (Aldrich)? 112 mg, 1.361 mmol) and DMF (1.36 ml). The reaction was stirred at 50° C. for 3 hrs. The mixture was diluted with water and Ethyl Acetate. The organic portion was collected, dried with sodium sulfate, filtered, and concentrated. The crude material was purified via column chromatography (RediSep Gold 40 g, gradient elution 10-75% [3:1 EtOAc/EtOH]:Heptane to give (P)-1-(4-(cyclopentylethynyl)-5-fluoro-2-methoxyphenyl)-N-(isoxazol-3-yl)-2-oxo-1,2-dihydroquinoline-6-sulfonamide (45 mg, 0.089 mmol, 32.6% yield) as an off-white solid. $^1$H NMR (400 MHz, DMSO-d$_6$) δ ppm 11.60 (br. s, 1H) 8.67 (d, J=1.81 Hz, 1H) 8.30-8.38 (m, 1H) 8.15 (d, J=9.69 Hz, 1H) 7.76 (dd, J=8.97, 2.23 Hz, 1H) 7.39 (d, J=9.17 Hz, 1H) 7.26 (d, J=6.38 Hz, 1H) 6.70-6.79 (m, 2H) 6.39 (d, J=1.76 Hz, 1H) 3.60 (s, 3H) 2.85-2.89 (m, 1H) 1.91-1.99 (m, 2H) 1.51-1.73 (m, 6H). m/z (ESI) 508.0 (M+H)$^+$.

BIOLOGICAL EXAMPLES

The following assays were used in testing the exemplary compounds of the invention. Data for those examples tested in accordance with the procedures described below are presented in Table 1 below.

Nav 1.7 or Nav 1.5 IWQ In Vitro Assay

HEK 293 Cells stably transfected with either Nav 1.7 or Nav 1.5 were recorded in population patch-clamp mode with the IonWorks® Quattro automated electrophysiology system in accordance with the manufacturer's specifications (Molecular Devices, LLC, Sunnyvale, Calif.). Sodium channel currents were measured in response to a train of depolarizations that induced successively greater inactivation.

Cells were held at −110 mV for three seconds (Nav 1.7) or half a second (Nav 1.5) from a holding voltage of −15 mV, then put through a series of 26 pulses of 150 msec duration to −20 mV at a frequency of 5 Hz. Cells were then left unclamped for a period of 3 to 8 minutes while a single concentration of test compound was added. Cells were then reclamped and put through the same voltage protocol. Current at the end of the 26$^{th}$ pulse to −20 mV was subtracted from the peak current evoked by the 26$^{th}$ pulse to −20 mV to correct for leak current. Percent block was calculated for each concentration in duplicate, and IC$_{50}$ curves were fitted to percent block as a function of concentration.

Nav 1.7 In Vitro PX Assay

HEK 293 cells stably transfected with human Nav1.7 were recorded in whole cell voltage clamp mode with the PatchXpress automated electrophysiology system (Molecular Devices, LLC, Sunnyvale, Calif.). Compound effects were measured on a partially inactivated state of the sodium channel. Cells were clamped to a holding potential yielding 20 to 50% inactivation. To elicit sodium current, channels were activated by pulsing to −10 mV for 20 msec. This voltage protocol was repeated at a rate of 0.1 Hz throughout the experiment. A single concentration of test compound was applied to cells for a duration of 3 minutes. Peak sodium current was measured at the end of the compound addition period to determine percent inhibition. Three to five cells were tested per concentration, and IC$_{50}$ curves were fitted to percent inhibition as a function of concentration. Data for compounds representative of the invention are presented in the Tables herein.

Nav 1.5 In Vitro PX Assay 293 cells stably transfected with Nav 1.5 were recorded in whole cell voltage clamp mode with the PatchXpress automated electrophysiology system according the manufacturer's specifications (Molecular Devices, LLC, Sunnyvale, Calif.). Cells were held at a holding potential of −50 mV to inactivate sodium channels. To elicit sodium currents the voltage was changed to −120 mV to recover a portion of the channels, followed by delivery of test pulses of 20 msec duration to 0 mV, at 0.1 Hz. A single concentration of test compound was applied to cells for a duration of 5 minutes. Peak sodium current was measured at the end of the compound addition period to determine percent inhibition. A minimum of two cells were tested per concentration. IC$_{50}$ curves were fitted to percent inhibition as a function of concentration. Data for compounds representative of the invention are presented in the Tables herein.

The compounds of the present invention may also be tested in the following in vivo assays.

Rat Formalin Model of Persistent Pain

On the test day, animals (Naïve, male Sprague Dawley rats) weighing between 260-300 g at the start of testing can be obtained from Harlan (Indianapolis, Ind.). All animals may be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. Animals are pretreated with the appropriate test compound either by oral gavage or intraperitoneal injection at the desired pretreatment time (typically two hours before test onset) and then returned to their home cages. After dosing and at least 30 minutes prior to test onset, animals can be acclimated to the individual testing chambers. At test time, each animal can be gently wrapped in a towel with the left hindpaw exposed. A dilute solution of formalin (2.5%) in phosphate buffered saline can be injected subcutaneously into the dorsal surface of the left hindpaw in a volume to 50 μL with a 30 g needle. Immediately following injection, a small metal band can be affixed to the plantar side of the left hindpaw with a drop of LOCTITE (adhesive). Animals may be then placed into the testing chambers and the number of flinches can be recorded between 10 to 40 minutes after formalin injection. A flinch is defined as a quick and spontaneous movement of the injected hindpaw not associated with ambulation. Flinches can be quantified with the aid of the Automated Nociception Analyzer built by the University of California, San Diego Department of Anesthesiology. Individual data can be expressed as a % maximal potential effect (% MPE) calculated with the following formula:

(−(Individual score−Vehicle average score)/Vehicle average score))*100=% MPE

Statistical analysis can be performed by analysis of variance (ANOVA), with post-hoc analysis using Bonferroni compared to the vehicle group for a significant main effect. Data can be represented as mean % MPE+/−standard error for each group.

Rat Open Field Assay

On the test day, animals (Naïve, male Sprague Dawley rats) weighing between 260-300 g at the start of testing may be obtained from Harlan (Indianapolis, Ind.). All animals can be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. In a room separate from the testing room, animals can be pretreated with the appropriate test compound either by oral gavage or intraperitoneal injection at the desired pretreatment time (typically two hours before test onset) and then can be returned to their home cages until the pretreatment has elapsed. At test time, animal can be transferred to the open field testing room in their home cages. Each animal may be placed in a separate testing chamber and the motion tracking system is started. The house lights in the testing room should be turned off and the animals can be allowed to explore the novel open field for 30 minutes. An automated motion tracker, made by San Diego Instruments, San Diego, Calif., can be used to capture animal exploration with the aid of infrared photo beams to detect animal movement. These behaviors include basic movement and vertical rearing, which can be used as the primary endpoints for this assay. At the end of the test, house lights can be turned on and the animals should be removed from the testing apparatus. Data can be expressed as a percent change from the vehicle control using the following equation.

(1−(Test mean/Vehicle mean))*100=% Change.

Statistical analysis can be performed by analysis of variance (ANOVA), with post-hoc analysis using Dunnett to follow up significant main effects.

Mouse Formalin Model of Persistent Pain

Mice (Naïve, male C57Bl/6) weighing between 22-30 g at the start of testing were obtained from Harlan (Indianapolis, Ind.). All animals were housed under a 12/12 h light/dark cycle with lights on at 0630. Rodents were singly housed on solid bottom cages with corn cob bedding and had access to food and water ad libitum. Animals were allowed to habituate to the vivarium for at least five days before testing was begun and were brought into the testing room at least 30 minutes prior to dosing. Animals were pretreated with the appropriate test compound either by oral gavage or intraperitoneal injection at the desired pretreatment time (typically two hours before test onset) and then returned to their home cages. After dosing and at least 5 minutes prior to test onset, animals were acclimated to the individual testing chambers. At test time, each animal was gently wrapped in a cloth glove with the left hind paw exposed. A dilute solution of formalin (2%) in phosphate buffered saline was injected subcutaneously into the dorsal surface of the left hind paw in a volume to 20 μL with a 30 g needle. Animals were then placed into the observation chambers and the behaviors were recorded for 60 minutes following the formalin injection. A pain-like behavior was defined as licking and/or non-weight bearing of the injected hind paw not associated with ambulation.

Statistical analysis was performed by analysis of variance (ANOVA), with post-hoc analysis using the Dunnett post-hoc test compared to the vehicle group for any significant main effect. Data were represented as mean+/−standard error for each group.

Mouse Open Field Assay

Mice (Naïve, male C57Bl/6) weighing between 22-30 g at the start of testing were obtained from Harlan (Indianapolis, Ind.). All animals were housed under a 12/12 h light/dark cycle with lights on at 0630. Rodents were singly housed on solid bottom cages with corn cob bedding and had access to food and water ad libitum. Animals were allowed to habituate to the vivarium for at least five days before testing was begun and were brought into the testing room at least 30 minutes prior to dosing. In a room separate from the testing room, animals were pretreated with the appropriate test compound either by oral gavage or intraperitoneal injection at the desired pretreatment time (typically two hours before test onset) and then returned to their home cages until the pretreatment has elapsed. At test time, animal were transferred to the open field testing room in their home cages. Each animal was placed in a separate testing chamber and the motion tracking system was started. The house lights in the testing room were turned off and the animals were allowed to explore the novel open field for 30 minutes. An automated motion tracker, made by Kinder Scientific, Poway, Calif., was used to capture animal exploration with the aid of infrared photo beams to detect animal movement. These behaviors include basic movement and vertical rearing, which were used as the primary endpoints for this assay. At the end of the test, house lights were turned on and the animals were removed from the testing apparatus.

Statistical analysis was performed by analysis of variance (ANOVA), with post-hoc analysis using the Dunnett post-hoc test compared to the vehicle group for any significant main effect. Data were represented as mean+/−standard error for each group. Data was also expressed as a percent change from the vehicle control using the following equation:

(1−(Test mean/Vehicle mean))*100=% Change.

CFA-Thermal Assay

Animals (Naïve, male Sprague Dawley rats) weighing between 260-300 g at the start of testing) can be obtained from Harlan (Indianapolis, Ind.). All animals can be housed under a 12/12 h light/dark cycle with lights on at 0600. Rodents may be housed two to a cage on solid bottom cages with corn cob bedding with access to food and water ad libitum. Animals can be allowed to habituate to the vivarium for at least five days before testing was begun and may be brought into the testing room at least 30 minutes prior to dosing. The Complete Freund's Adjuvant (CFA)-thermal assay may use a three continuous day testing schedule consisting of a habituation day, a baseline day, and a test day. On day 1, animals can be brought into the testing room, labeled, and placed in their individual testing boxes on the testing apparatus. Animals may be allowed to explore this environment for at least an hour without actually being tested. After habituating, animals can be placed back in their home cages and returned to the vivarium. On day 2, animals can be brought back into the testing room and placed on the testing apparatus and allowed to calm down (typically 30-45 minutes). A basal thermal threshold should be then taken with the following procedure: once calm, a Ugo Basile plantar device is placed under the animals left hindpaw; the start button is depressed turning on a steadily increasing thermal source and a timer; when the animal reaches its thermal threshold it will flinch its hindpaw, stopping the timer and the thermal stimulus. This latency to flinch can be recorded three times for each animal, with at least 5 minutes between trials, and the mean score can be used as the animal's baseline threshold. After testing, animals can be injected intraplantarly with a 25 μg/50 μl of complete Freund's adjuvant into the left hindpaw. Animals are then retuned to their home cages and returned to the vivarium. On test day, animals can be again placed on the thermal testing apparatus and their post-CFA baselines obtained with the procedure outlined above. Animals can be pretreated with the appropriate test compound either by oral gavage or intraperitoneal injection at the desired pretreatment time (typically two hours before test onset) and then can be returned to their home cages. Thirty minutes prior to testing, animals can be placed on the apparatus again. Once the pretreatment time has elapsed, animals can be again tested with the procedure above. Data may be expressed as a percent maximal potential effect with the following formula:

((Post-Drug Mean−Pre-Drug Mean)/(Baseline Mean−Pre-Drug Mean))*100=% MPE

Statistical analysis can be performed by analysis of variance (ANOVA), with post-hoc analysis using Bonferroni compared to the vehicle group for a significant main effect. Data can be represented as mean % MPE+/−standard error for each group.

Spinal Nerve Ligation (Chung)

Animals (Naïve, male Sprague Dawley rats) weighing between 150-200 g at the start of first time testing can be obtained from Harlan (Indianapolis, Ind.). All animals may be housed under a 12/12 h light/dark cycle with lights on at 0600. Rodents can be housed two to a cage on solid bottom cages with corn cob bedding with access to food and water ad libitum. Animals may be allowed to habituate to the vivarium for at least five days before testing is begun. Surgery may be then performed based on the method described by Kim and Chung (1992). Briefly, animals can be placed under isoflurane anesthesia and placed in a sterile surgical field. The area of the lumbar spine is excised and the spinal nerves at L4-L5 are exposed. The L5 spinal nerve is identified and tightly ligated with 5-0 silk suture. The muscle may be closed with absorbable suture and the skin with wound clip. Animals may be returned to the vivarium for 7-14 days and monitored daily. On test day, animals can be brought into the testing room and placed on a wire mesh floor in individual testing chambers. They may be allowed to acclimate to the chambers until they are calm. A series of Semmes-Weinstein monofilaments (von Frey hairs) with calibrated bending forces are then applied to determine a hyperalgesic baseline following the method set forth by Chaplan et al. (1994). Briefly, filaments are applied with an increasing force (if there was not reaction to the previous stimulus) or decreasing force (if there was a reaction to the previous stimulus) until a baseline value is reached. Animals are then pretreated with the appropriate test compound either by oral gavage or intraperitoneal injection at the desired pretreatment time (typically two hours before test onset) and then returned to their home cages. Thirty minutes prior to testing, animals are placed on the apparatus again. After the pretreatment time had elapsed, the procedure above is repeated to determine drug efficacy. Data can be expressed as the mean gram force to elicit a nociceptive behavior. Statistical analysis can be performed by analysis of variance (ANOVA), with post-hoc analysis using Bonferroni compared to the vehicle group for a significant main effect.

Table 1 provides data for compounds exemplified in the present application and priority document thereof, as representative compounds of the present invention, as follows: compound name (as named by ACD software, version 12; while the compound names in the written examples presented herein were named using ChemDraw Ultra version 12); and biological data including in-vitro Nav 1.7 PX data ($IC_{50}$ in uM), Nav 1.7 IWQ data ($IC_{50}$ in uM), HLM data in vitro (µL/(min·mg)), and Human PXR @ 2 uM POC S (%), where available. Ex. # refers to Example No. Compounds of the present invention show favorable activities against hNav1.7 as well as RLM and human PXR data.

TABLE 1

BIOLOGICAL DATA

| Ex. No. | COMPOUND NAME | hNav1.7 IWQ $IC_{50}$ (µM) | hNav1.7 PX $IC_{50}$ (µM) | RLM in vitro (µL/(min · mg)) | human PXR @ 2 uM POCS (%) |
|---|---|---|---|---|---|
| 1 | 1-(4-((4,4-difluorocyclohexyl)ethynyl)-5-fluoro-2-methoxyphenyl)-N-3-isoxazolyl-2-oxo-1,2-dihydro-6-quinolinesulfonamide | 0.0033 | 0.0446 | <14.0 | 2.36 |
| 2 | 1-(5-fluoro-2-methoxy-4-(4,4,4-trifluoro-3,3-dimethyl-1-butyn-1-yl)phenyl)-N-3-isoxazolyl-2-oxo-1,2-dihydro-6-quinolinesulfonamide | 0.0012 | 0.0278 | <14.0 | 1.38 |
| 3 | 1-(4-(cyclopentylethynyl)-2-methoxyphenyl)-N-3-isoxazolyl-2-oxo-1,2-dihydro-6-quinolinesulfonamide | 0.0075 | 0.0497 | 39 | −1.44 |
| 4 | Mixture of 1-(5-fluoro-2-methoxy-4-(((1R,2S)-2-(trifluoromethyl)cyclopropyl)ethynyl)phenyl)-N-3-isoxazolyl-2-oxo-1,2-dihydro-6-quinolinesulfonamide, 1-(5-fluoro-2-methoxy-4-(((1S,2S)-2-(trifluoromethyl)cyclopropyl)ethynyl)phenyl)-N-3-isoxazolyl-2-oxo-1,2-dihydro-6-quinolinesulfonamide | 0.0070 | 0.0578 | <14.0 | 13.54 |
| 4A | 1-(5-fluoro-2-methoxy-4-(((1R,2S)-2-(trifluoromethyl)cyclopropyl)ethynyl)phenyl)-N-3-isoxazolyl-2-oxo-1,2-dihydro-6-quinolinesulfonamide | 0.0068 | 0.2104 | <14.0 | 23.19 |
| 4B | 1-(5-fluoro-2-methoxy-4-(((1R,2R)-2-(trifluoromethyl)cyclopropyl)ethynyl)phenyl)-N-3-isoxazolyl-2-oxo-1,2-dihydro-6-quinolinesulfonamide | 0.0055 | 0.1393 | <14.0 | −3.81 |
| 5 | 1-(5-fluoro-2-methoxy-4-((1-(trifluoromethyl)cyclopropyl)ethynyl)phenyl)-N-3-isoxazolyl-2-oxo-1,2-dihydro-6-quinolinesulfonamide | 0.0080 | 0.0620 | <14.0 | 1.73 |
| 6 | 1-(5-chloro-4-(cyclopentylethynyl)-2-methoxyphenyl)-N-3-isoxazolyl-2-oxo-1,2-dihydro-6-quinolinesulfonamide | 0.0100 | 0.0186 | 58 | −3.96 |

TABLE 1-continued

BIOLOGICAL DATA

| Ex. No. | COMPOUND NAME | hNav1.7 IWQ IC$_{50}$ (μM) | hNav1.7 PX IC$_{50}$ (μM) | RLM in vitro (μL/(min · mg)) | human PXR @ 2 uM POCS (%) |
|---|---|---|---|---|---|
| 7 | Mixture of 1-(4-(((1R)-3,3-difluorocyclohexyl)ethynyl)-5-fluoro-2-methoxyphenyl)-N-3-isoxazolyl-2-oxo-1,2-dihydro-6-quinolinesulfonamide, 1-(4-(((1S)-3,3-difluorocyclohexyl)ethynyl)-5-fluoro-2-methoxyphenyl)-N-3-isoxazolyl-2-oxo-1,2-dihydro-6-quinolinesulfonamide | 0.0078 | 0.0667 | <14.0 | −0.78 |
| 8 | 1-(4-(cyclopentylethynyl)-5-fluoro-2-methoxyphenyl)-2-oxo-N-3-pyridazinyl-1,2-dihydro-6-quinolinesulfonamide | 0.00973 | 0.033752 | 63.2 | 13.32 |
| 9 | 1-(5-fluoro-2-methoxy-4-((1-(2,2,2-trifluoroethoxy)cyclopentyl)ethynyl)phenyl)-N-3-isoxazolyl-2-oxo-1,2-dihydro-6-quinolinesulfonamide | 0.00895 | 0.01933 | 32.2 | 11.80 |
| 10 | 1-(4-(cyclopentylethynyl)-5-fluoro-2-methoxyphenyl)-N-3-isoxazolyl-2-oxo-1,2-dihydro-6-quinolinesulfonamide | 0.00453 | 0.017295 | 39.8 | 2.94 |

The foregoing invention has been described in some detail by way of illustration and example, for purposes of clarity and understanding. Those skilled in the art understand that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited herein are hereby incorporated by reference in their entirety for all purposes to the same extent as if each individual patent, patent application or publication were so individually denoted.

What is claimed is:

1. A compound of Formula I, an enantiomer, diastereoisomer, atropisomer thereof, a mixture thereof, or a pharmaceutically acceptable salt thereof,

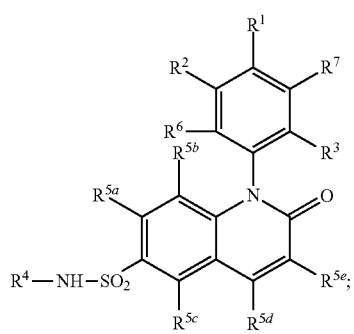

(I)

wherein:

$R^1$ is an ethynyl substituted by an $C_{4-8}$ alk or a cyclopropyl, cyclobutyl, or cyclohexyl ring; wherein said $C_{4-8}$ alk is substituted by 1, 2, 3, or 4 halo; and wherein said cyclopropyl, cyclobutyl, or cyclohexyl ring is substituted by 1, 2, 3, or 4 halo or $C_{1-4}$haloalk;

$R^2$ is H, halo, $C_{1-6}$alk, or $C_{1-6}$haloalk;

$R^3$ is $C_{1-6}$alk, $C_{1-4}$haloalk, —O—$C_{1-6}$alk, or —CN;

$R^4$ is isoxazolyl or pyrimidinyl;

Each of $R^6$ and $R^7$ is hydrogen; and

Each of $R^{5a}$; $R^{5b}$; $R^{5c}$; $R^{5d}$; and $R^{5e}$ is independently hydrogen or halo.

2. The compound according to claim 1, an enantiomer, diastereoisomer, atropisomer thereof, a mixture thereof, or a pharmaceutically acceptable salt thereof, wherein $R^1$ is selected from —C≡C—CF$_3$, —C≡C—C(CH$_3$)$_2$—CF$_3$, —C≡C— cyclopropyl-CF$_3$, —C≡C-cyclopentyl (wherein said cyclopentyl is unsubstituted or is substituted by —O—CH$_2$—CF$_3$), or —C≡C-cyclohexyl- (wherein said cyclohexyl is substituted by 2 F atoms).

3. The compound according to claim 1, an enantiomer, diastereoisomer, atropisomer thereof, a mixture thereof, or a pharmaceutically acceptable salt thereof, wherein $R^2$ is H, fluoro, chloro, methyl, CF$_3$, CHF$_2$, or CH$_2$F.

4. The compound according to claim 1, an enantiomer, diastereoisomer, atropisomer thereof, a mixture thereof, or a pharmaceutically acceptable salt thereof, wherein $R^3$ is methoxy.

5. The compound according to claim 1, an enantiomer, diastereoisomer, atropisomer thereof, a mixture thereof, or a pharmaceutically acceptable salt thereof, wherein $R^4$ is an isoxazolyl.

6. The compound according to claim 1, an enantiomer, diastereoisomer, atropisomer thereof, a mixture thereof, or a pharmaceutically acceptable salt thereof, wherein $R^4$ is a pyrimidinyl.

7. The compound according to claim 1, an enantiomer, diastereoisomer, atropisomer thereof, a mixture thereof, or a pharmaceutically acceptable salt thereof, wherein each of $R^{5a}$; $R^{5b}$; $R^{5c}$; $R^{5d}$; and $R^{5e}$ is hydrogen.

8. The compound according to claim 1, an enantiomer, diastereoisomer, atropisomer thereof, a mixture thereof, or a pharmaceutically acceptable salt thereof, which is selected from the group consisting of

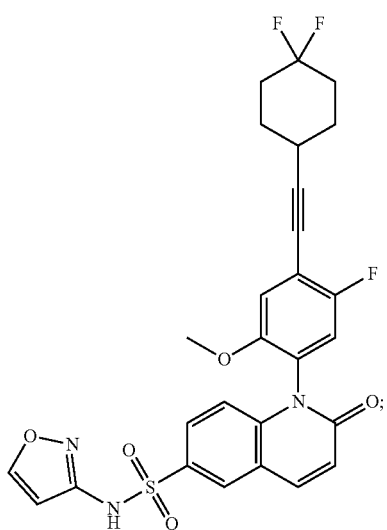
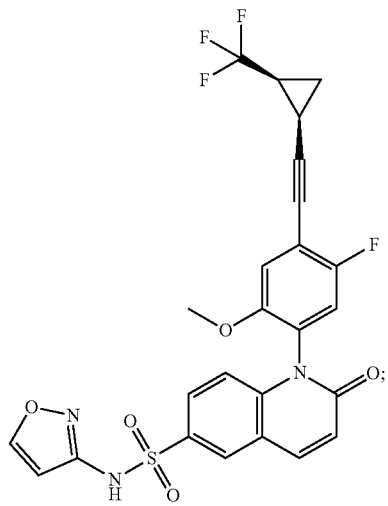
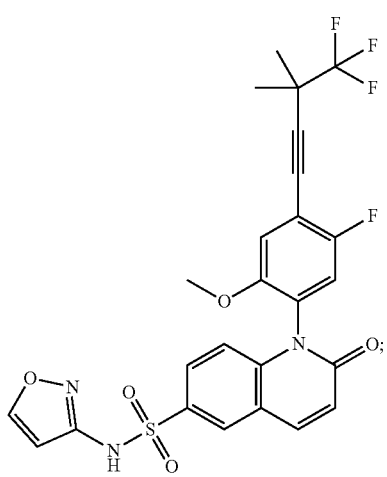
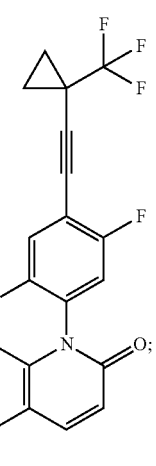
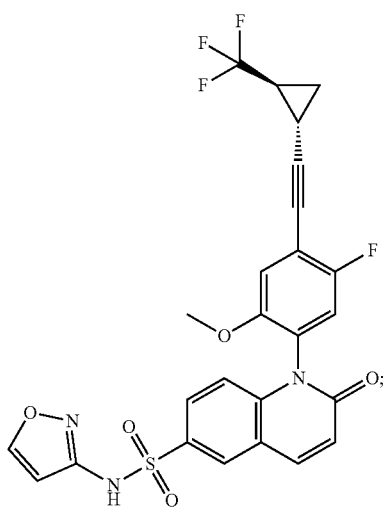
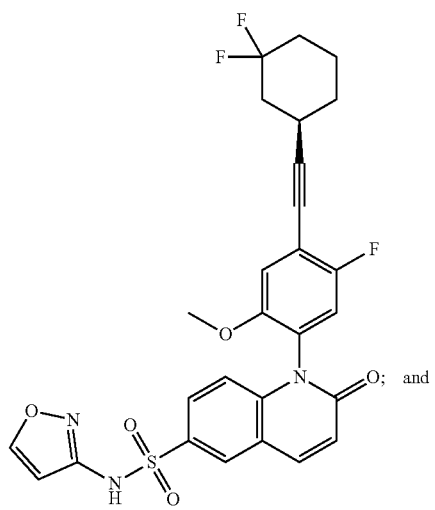

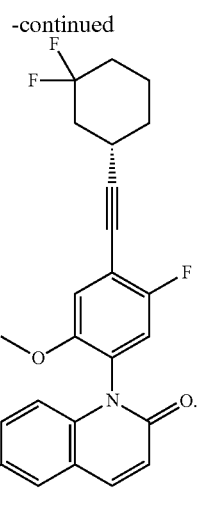

9. The compound according to claim 1, an enantiomer, diastereoisomer, atropisomer thereof, a mixture thereof, or a pharmaceutically acceptable salt thereof, wherein said atropisomer is a P atropisomer.

10. A pharmaceutical composition comprising a compound according to claim 1, an enantiomer, diastereoisomer, atropisomer thereof, a mixture thereof, or a pharmaceutically acceptable salt thereof, and a pharmaceutically acceptable excipient.

11. A method of treating pain, cough, or itch mediated by Nav 1.7, the method comprising administering to a patient in need thereof a therapeutically effective amount of a compound according to claim 1, an enantiomer, diastereoisomer, atropisomer thereof, a mixture thereof, or a pharmaceutically acceptable salt thereof.

12. The method according to claim 11; wherein the pain is selected from chronic pain, acute pain, neuropathic pain, pain associated with rheumatoid arthritis, pain associated with osteoarthritis or pain associated with cancer.

13. The method according to claim 11; wherein the cough is selected from post viral cough, viral cough, or acute viral cough.

14. The compound according to claim 8, an enantiomer, diastereoisomer, atropisomer thereof, or a pharmaceutically acceptable salt thereof, which is

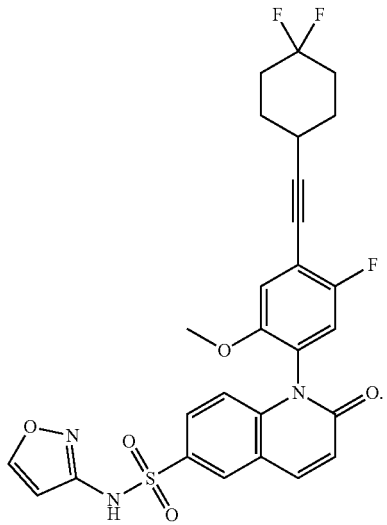 [SMILES: COc1cc(C#CC2CCC(F)(F)CC2)c(F)cc1-n1c(=O)ccc2cc(S(=O)(=O)Nc3ccon3)ccc21]

15. The compound according to claim 8, an enantiomer, diastereoisomer, atropisomer thereof, or a pharmaceutically acceptable salt thereof, which is

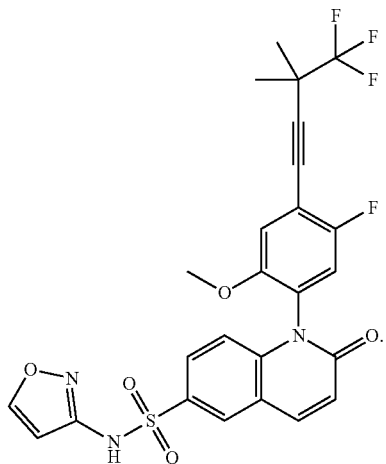 [SMILES: COc1cc(C#CC(C)(C)C(F)(F)F)c(F)cc1-n1c(=O)ccc2cc(S(=O)(=O)Nc3ccon3)ccc21]

16. The compound according to claim 8, an enantiomer, diastereoisomer, atropisomer thereof, or a pharmaceutically acceptable salt thereof, which is

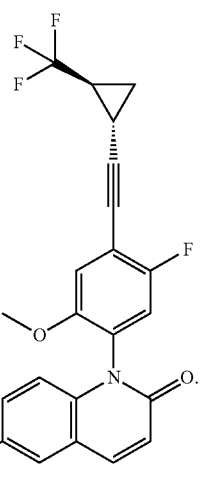

17. The compound according to claim 8, an enantiomer, diastereoisomer, atropisomer thereof, or a pharmaceutically acceptable salt thereof, which is

18. The compound according to claim 8, an enantiomer, diastereoisomer, atropisomer thereof, or a pharmaceutically acceptable salt thereof, which is

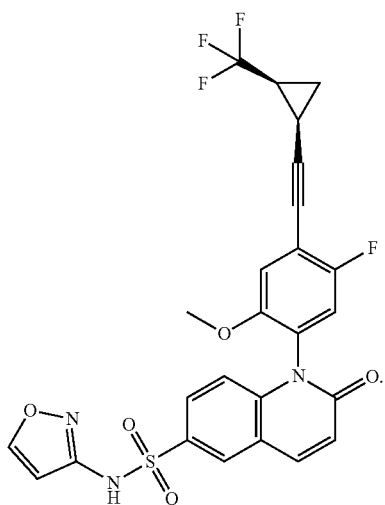 [SMILES: COc1cc(C#C[C@@H]2C[C@@H]2C(F)(F)F)c(F)cc1-n1c(=O)ccc2cc(S(=O)(=O)Nc3ccon3)ccc21]

19. The compound according to claim 8, an enantiomer, diastereoisomer, atropisomer thereof, or a pharmaceutically acceptable salt thereof, which is

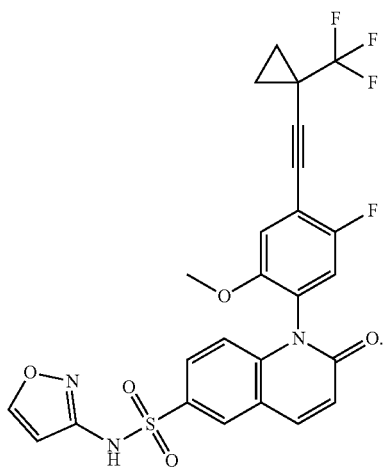 [SMILES: COc1cc(C#CC2(C(F)(F)F)CC2)c(F)cc1-n1c(=O)ccc2cc(S(=O)(=O)Nc3ccon3)ccc21]

20. The compound according to claim 8, an enantiomer, diastereoisomer, atropisomer thereof, or a pharmaceutically acceptable salt thereof, which is

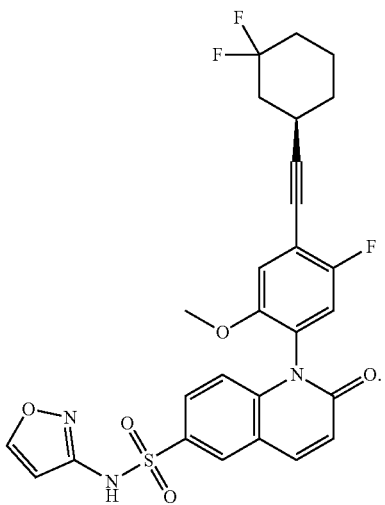 [SMILES: COc1cc(C#C[C@@H]2CCCC(F)(F)C2)c(F)cc1-n1c(=O)ccc2cc(S(=O)(=O)Nc3ccon3)ccc21]

* * * * *